United States Patent
Balog et al.

(10) Patent No.: US 11,139,156 B2
(45) Date of Patent: Oct. 5, 2021

(54) IN VIVO ENDOSCOPIC TISSUE IDENTIFICATION TOOL

(71) Applicant: Micromass UK Limited, Wilmslow (GB)

(72) Inventors: Julia Balog, Solymar (HU); Tamas Karancsi, Budapest (HU); Steven Derek Pringle, Darwen (GB); Zoltan Takats, Cambridge (GB); James Kinross, London (GB); Jeremy K Nicholson, Croydon (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/555,888

(22) PCT Filed: Mar. 7, 2016

(86) PCT No.: PCT/GB2016/050623
§ 371 (c)(1),
(2) Date: Sep. 5, 2017

(87) PCT Pub. No.: WO2016/142693
PCT Pub. Date: Sep. 15, 2016

(65) Prior Publication Data
US 2018/0049643 A1    Feb. 22, 2018

(30) Foreign Application Priority Data

Mar. 6, 2015  (GB) ...................................... 1503863
Mar. 6, 2015  (GB) ...................................... 1503864
(Continued)

(51) Int. Cl.
*A61B 10/02*   (2006.01)
*H01J 49/04*   (2006.01)
(Continued)

(52) U.S. Cl.
CPC ............ *H01J 49/049* (2013.01); *A61B 1/041* (2013.01); *A61B 1/2736* (2013.01);
(Continued)

(58) Field of Classification Search
CPC ................ A61B 10/00; A61B 10/0283; A61B 2010/0083; A61B 2017/320069;
(Continued)

(56) References Cited

U.S. PATENT DOCUMENTS 525,799 A     9/1894  Rymes
3,479,545 A   11/1969 Wilson et al.
(Continued)

FOREIGN PATENT DOCUMENTS

CA  2527886 A1  12/2004
CA  2876731 A1  12/2013
(Continued)

OTHER PUBLICATIONS

Schafer, Karl-Christian, et al. "In vivo, in situ tissue analysis using rapid evaporative ionization mass spectrometry." Angewandte Chemie International Edition 48.44 (2009): 8240-8242.*
(Continued)

*Primary Examiner* — Wyatt A Stoffa
(74) *Attorney, Agent, or Firm* — Kacvinsky Daisak Bluni PLLC

(57) ABSTRACT

An apparatus is disclosed including a tool comprising a first device for generating aerosol from a target, the first device being deployed through an opening in a tubing of the tool, wherein the tubing is provided with aspiration ports or fenestrations such that the generated aerosol is aspirated into the tubing via the aspiration ports or fenestrations. The aspirated aerosol is then transferred to a mass spectrometer for subsequent mass analysis.

15 Claims, 16 Drawing Sheets

(30) Foreign Application Priority Data

| | | |
|---|---|---|
| Mar. 6, 2015 | (GB) | 1503867 |
| Mar. 6, 2015 | (GB) | 1503876 |
| Mar. 6, 2015 | (GB) | 1503877 |
| Mar. 6, 2015 | (GB) | 1503878 |
| Mar. 6, 2015 | (GB) | 1503879 |
| Sep. 9, 2015 | (GB) | 1516003 |
| Oct. 16, 2015 | (GB) | 1518369 |

(51) Int. Cl.

| | |
|---|---|
| A61B 17/32 | (2006.01) |
| A61B 18/00 | (2006.01) |
| A61B 18/14 | (2006.01) |
| A61B 18/20 | (2006.01) |
| G01N 3/00 | (2006.01) |
| G01N 9/00 | (2006.01) |
| G01N 33/68 | (2006.01) |
| H01J 49/00 | (2006.01) |
| H01J 49/06 | (2006.01) |
| H01J 49/16 | (2006.01) |
| A61B 90/13 | (2016.01) |
| A61B 1/04 | (2006.01) |
| A61B 1/273 | (2006.01) |
| A61B 5/00 | (2006.01) |
| A61B 5/01 | (2006.01) |
| A61B 5/0507 | (2021.01) |
| A61B 5/055 | (2006.01) |
| A61B 6/03 | (2006.01) |
| A61B 8/13 | (2006.01) |
| A61B 10/00 | (2006.01) |
| A61B 17/00 | (2006.01) |
| A61B 18/04 | (2006.01) |
| A61B 18/18 | (2006.01) |
| A61F 13/38 | (2006.01) |
| C12Q 1/02 | (2006.01) |
| C12Q 1/04 | (2006.01) |
| C12Q 1/18 | (2006.01) |
| C12Q 1/24 | (2006.01) |
| G01N 1/22 | (2006.01) |
| G01N 27/622 | (2021.01) |
| G01N 27/624 | (2021.01) |
| G01N 30/72 | (2006.01) |
| G01N 33/487 | (2006.01) |
| G01N 33/92 | (2006.01) |
| H01J 49/02 | (2006.01) |
| H01J 49/10 | (2006.01) |
| H01J 49/14 | (2006.01) |
| H01J 49/24 | (2006.01) |
| H01J 49/26 | (2006.01) |
| G16B 20/00 | (2019.01) |
| G16H 10/40 | (2018.01) |
| G16H 15/00 | (2018.01) |
| G16H 50/20 | (2018.01) |
| A61B 1/00 | (2006.01) |
| A61B 1/31 | (2006.01) |
| A61B 5/145 | (2006.01) |

(52) U.S. Cl.
CPC .......... *A61B 5/0066* (2013.01); *A61B 5/0075* (2013.01); *A61B 5/015* (2013.01); *A61B 5/055* (2013.01); *A61B 5/0507* (2013.01); *A61B 6/032* (2013.01); *A61B 6/037* (2013.01); *A61B 8/13* (2013.01); *A61B 10/00* (2013.01); *A61B 10/0041* (2013.01); *A61B 10/0233* (2013.01); *A61B 10/0283* (2013.01); *A61B 17/00* (2013.01); *A61B 17/320068* (2013.01); *A61B 18/00* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/622* (2013.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *H01J 49/0004* (2013.01); *H01J 49/0027* (2013.01); *H01J 49/0031* (2013.01); *H01J 49/0036* (2013.01); *H01J 49/025* (2013.01); *H01J 49/044* (2013.01); *H01J 49/0404* (2013.01); *H01J 49/0409* (2013.01); *H01J 49/0422* (2013.01); *H01J 49/0445* (2013.01); *H01J 49/0459* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 33/48735* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G16B 20/00* (2019.02); *G16H 10/40* (2018.01); *G16H 15/00* (2018.01); *G16H 50/20* (2018.01)

(58) Field of Classification Search
CPC ............... H01J 49/0004; H01J 49/0027; H01J 49/0031; H01J 49/0036; H01J 49/025; H01J 49/0404; H01J 49/0422; H01J 49/0445; H01J 49/0459; H01J 49/0463; H01J 49/0468; H01J 49/049; H01J 49/061; H01J 49/068; H01J 49/10; H01J 49/14; H01J 49/16; H01J 49/164; H01J 49/24; H01J 49/26; H01J 49/49; H01J 49/0409; H01J 49/1049; G01N 1/2202; G01N 2001/2223; G01N 2333/195
See application file for complete search history.

(56) References Cited

U.S. PATENT DOCUMENTS

| | | |
|---|---|---|
| 3,770,954 A | 11/1973 | Davis |
| 4,408,125 A | 10/1983 | Meuzelaar |
| H414 H | 1/1988 | Young et al. |
| 4,835,383 A | 5/1989 | Mahoney et al. |
| 4,845,367 A | 7/1989 | Kmirav et al. |
| 4,883,958 A | 11/1989 | Vestal |
| 4,935,624 A | 6/1990 | Henion et al. |
| 5,033,541 A | 7/1991 | D'Silva |
| 5,053,343 A | 10/1991 | Vora et al. |
| 5,210,412 A | 5/1993 | Levis et al. |
| 5,257,991 A | 11/1993 | Fletcher et al. |

(56) References Cited

U.S. PATENT DOCUMENTS

| | | |
|---|---|---|
| 5,306,977 A | 4/1994 | Hayashi |
| 5,374,755 A | 12/1994 | Neue et al. |
| 5,454,274 A | 10/1995 | Zhu |
| 5,509,916 A * | 4/1996 | Taylor ................... A61B 18/14 606/10 |
| 5,559,326 A | 9/1996 | Goodley et al. |
| 5,663,561 A * | 9/1997 | Franzen ............. H01J 49/0463 250/282 |
| 5,696,352 A | 12/1997 | Kourimsky |
| 5,800,597 A | 9/1998 | Perrotta et al. |
| 5,828,062 A | 10/1998 | Jarrell et al. |
| 5,830,214 A | 11/1998 | Flom et al. |
| 5,836,909 A | 11/1998 | Cosmescu |
| 5,969,352 A | 10/1999 | French et al. |
| 5,989,015 A | 11/1999 | Guerin et al. |
| 6,032,673 A | 3/2000 | Savage et al. |
| 6,333,632 B1 | 12/2001 | Yang et al. |
| 6,348,688 B1 | 2/2002 | Vestal |
| 6,825,464 B2 | 11/2004 | De La Mora |
| 6,998,622 B1 | 2/2006 | Wang et al. |
| 7,238,936 B2 | 7/2007 | Okamura et al. |
| 7,247,845 B1 * | 7/2007 | Gebhardt ................... F03H 1/00 250/281 |
| 7,329,253 B2 | 2/2008 | Brounstein et al. |
| 7,335,897 B2 | 2/2008 | Takats et al. |
| 7,365,309 B2 | 4/2008 | Denny et al. |
| 7,517,348 B2 | 4/2009 | Vetter et al. |
| 7,564,028 B2 | 7/2009 | Vestal |
| 7,718,958 B2 | 5/2010 | Shiea et al. |
| 7,828,948 B1 | 11/2010 | Hatch et al. |
| 7,947,039 B2 | 5/2011 | Sartor |
| 7,960,711 B1 | 6/2011 | Sheehan et al. |
| 8,156,151 B2 | 4/2012 | Sidman |
| 8,193,487 B2 | 6/2012 | Briglin et al. |
| 8,232,520 B2 | 7/2012 | Cristoni |
| 8,253,098 B2 | 8/2012 | Hiraoka et al. |
| 8,286,260 B2 | 10/2012 | Vertes et al. |
| 8,314,382 B2 | 11/2012 | Takats |
| 8,334,504 B2 | 12/2012 | Finlay et al. |
| 8,431,409 B1 | 4/2013 | Meinhart et al. |
| 8,448,493 B2 | 5/2013 | McIntyre et al. |
| 8,481,922 B2 | 7/2013 | Musselman |
| 8,778,695 B2 | 7/2014 | Caprioli |
| 8,803,085 B2 | 8/2014 | Ouyang et al. |
| 8,834,462 B2 | 9/2014 | Johnson et al. |
| 8,970,840 B2 | 3/2015 | Kulkarni et al. |
| 8,980,577 B2 | 3/2015 | Maier |
| 9,046,448 B2 | 6/2015 | Takats |
| 9,053,914 B2 * | 6/2015 | Pringle ............... H01J 49/0022 |
| 9,082,603 B2 | 7/2015 | Bajic |
| 9,120,083 B2 | 9/2015 | Wyndham et al. |
| 9,255,907 B2 | 2/2016 | Heanue et al. |
| 9,281,174 B2 | 3/2016 | Takats |
| 9,287,100 B2 | 3/2016 | Szalay et al. |
| 9,709,529 B2 | 7/2017 | Takats |
| 9,731,219 B2 | 8/2017 | Wang et al. |
| 9,947,524 B2 | 4/2018 | Pringle et al. |
| 10,077,461 B2 | 9/2018 | Beaulieu et al. |
| 10,186,626 B2 | 1/2019 | Song et al. |
| 2002/0008871 A1 | 1/2002 | Poustka et al. |
| 2002/0070338 A1 | 6/2002 | Loboda |
| 2002/0076824 A1 | 6/2002 | Haglund, Jr. et al. |
| 2003/0001084 A1 | 1/2003 | Bateman et al. |
| 2003/0008404 A1 | 1/2003 | Tomita et al. |
| 2003/0015657 A1 | 1/2003 | Takada et al. |
| 2003/0042412 A1 | 3/2003 | Park |
| 2003/0080278 A1 | 5/2003 | Okada et al. |
| 2003/0119193 A1 | 6/2003 | Hess et al. |
| 2003/0135222 A1 | 7/2003 | Baska |
| 2003/0136918 A1 | 7/2003 | Hartley |
| 2003/0193023 A1 | 10/2003 | Marsh |
| 2004/0007673 A1 | 1/2004 | Coon et al. |
| 2004/0079881 A1 | 4/2004 | Fischer et al. |
| 2004/0124352 A1 | 7/2004 | Kashima et al. |
| 2004/0197899 A1 | 10/2004 | Gomez et al. |
| 2004/0217274 A1 | 11/2004 | Bai et al. |
| 2004/0235395 A1 | 11/2004 | Hashish et al. |
| 2005/0017091 A1 | 1/2005 | Olsen et al. |
| 2005/0032471 A1 | 2/2005 | Pfarr et al. |
| 2005/0061779 A1 | 3/2005 | Blumenfeld et al. |
| 2005/0067565 A1 | 3/2005 | Takada et al. |
| 2005/0072916 A1 | 4/2005 | Park |
| 2005/0074361 A1 | 4/2005 | Tanoshima et al. |
| 2005/0077644 A1 | 4/2005 | Bryan et al. |
| 2005/0124986 A1 * | 6/2005 | Brounstein ............ A61B 18/00 606/39 |
| 2005/0138861 A1 | 6/2005 | O'Connor |
| 2005/0154490 A1 | 7/2005 | Blaine et al. |
| 2005/0159765 A1 | 7/2005 | Moutafis et al. |
| 2005/0178962 A1 | 8/2005 | Guevremont et al. |
| 2005/0178975 A1 | 8/2005 | Glukhoy |
| 2005/0179366 A1 | 8/2005 | Rose et al. |
| 2005/0230634 A1 | 10/2005 | Bajic et al. |
| 2005/0230635 A1 | 10/2005 | Takats et al. |
| 2005/0258358 A1 | 11/2005 | Thakur |
| 2005/0269518 A1 | 12/2005 | Bajic et al. |
| 2005/0274885 A1 | 12/2005 | Brown et al. |
| 2006/0035570 A1 | 2/2006 | Chisum et al. |
| 2006/0054806 A1 | 3/2006 | Yamada et al. |
| 2006/0091308 A1 | 5/2006 | Boyle et al. |
| 2006/0097084 A1 | 5/2006 | Gromer et al. |
| 2006/0108539 A1 | 5/2006 | Franzen |
| 2006/0113463 A1 | 6/2006 | Rossier et al. |
| 2006/0122593 A1 | 6/2006 | Jun |
| 2006/0138321 A1 | 6/2006 | Ahem et al. |
| 2006/0145089 A1 | 7/2006 | Cristoni et al. |
| 2006/0186334 A1 | 8/2006 | Jolliffe et al. |
| 2006/0250138 A1 | 11/2006 | Sparkman et al. |
| 2006/0255264 A1 | 11/2006 | Belford |
| 2007/0023631 A1 | 2/2007 | Takats et al. |
| 2007/0023677 A1 | 2/2007 | Perkins et al. |
| 2007/0094389 A1 | 4/2007 | Nussey et al. |
| 2007/0114388 A1 * | 5/2007 | Ogawa ................... H01J 49/161 250/288 |
| 2007/0114394 A1 | 5/2007 | Combs et al. |
| 2007/0114437 A1 | 5/2007 | Kovtoun |
| 2007/0176113 A1 | 8/2007 | Shiea et al. |
| 2007/0181802 A1 | 8/2007 | Yamada et al. |
| 2008/0001081 A1 | 1/2008 | Jindai et al. |
| 2008/0015278 A1 | 1/2008 | Malik et al. |
| 2008/0042056 A1 | 2/2008 | Fischer et al. |
| 2008/0067352 A1 | 3/2008 | Wang |
| 2008/0073503 A1 | 3/2008 | Wu |
| 2008/0073512 A1 | 3/2008 | Siuzdak et al. |
| 2008/0132890 A1 * | 6/2008 | Woloszko ............ A61B 18/1482 606/41 |
| 2008/0149822 A1 | 6/2008 | Vertes et al. |
| 2008/0172075 A1 | 7/2008 | Ammann |
| 2008/0173809 A1 | 7/2008 | Wu |
| 2008/0234579 A1 | 9/2008 | Halevy-Politch et al. |
| 2008/0312651 A1 | 12/2008 | Pope et al. |
| 2009/0065714 A1 | 3/2009 | Keady |
| 2009/0082637 A1 | 3/2009 | Galperin |
| 2009/0126891 A1 | 5/2009 | Koivunen et al. |
| 2009/0159790 A1 | 6/2009 | Kostiainen et al. |
| 2009/0272893 A1 * | 11/2009 | Hieftje ................. H01J 49/0004 250/282 |
| 2009/0302211 A1 * | 12/2009 | Takats .................. H01J 49/0463 250/282 |
| 2010/0012830 A1 | 1/2010 | Cristoni |
| 2010/0072359 A1 | 3/2010 | Briglin et al. |
| 2010/0078550 A1 | 4/2010 | Wiseman et al. |
| 2010/0101304 A1 | 4/2010 | McIntyre et al. |
| 2010/0176290 A1 | 7/2010 | Vidal-De-Miguel |
| 2010/0186524 A1 | 7/2010 | Ariessohn et al. |
| 2010/0229263 A1 | 9/2010 | Vertes et al. |
| 2011/0036978 A1 | 2/2011 | Franzen |
| 2011/0049352 A1 * | 3/2011 | Ding .................... H01J 49/0463 250/282 |
| 2011/0059554 A1 | 3/2011 | Albers et al. |
| 2011/0066147 A1 | 3/2011 | He et al. |
| 2011/0087308 A1 | 4/2011 | Morgan et al. |
| 2011/0121173 A1 | 5/2011 | Koenig et al. |

(56) References Cited

U.S. PATENT DOCUMENTS

| | | | |
|---|---|---|---|
| 2011/0295250 A1* | 12/2011 | Johnson | A61B 18/042 606/41 |
| 2012/0018628 A1 | 1/2012 | Wuijckhuijse et al. | |
| 2012/0043460 A1 | 2/2012 | Wouters et al. | |
| 2012/0048264 A1* | 3/2012 | Finlay | A61M 13/003 128/200.14 |
| 2012/0074306 A1 | 3/2012 | Jesse et al. | |
| 2012/0079894 A1 | 4/2012 | Van Berkel et al. | |
| 2012/0080592 A1 | 4/2012 | Wiseman et al. | |
| 2012/0085649 A1 | 4/2012 | Sano et al. | |
| 2012/0119079 A1 | 5/2012 | Ouyang et al. | |
| 2012/0149009 A1 | 6/2012 | Levis et al. | |
| 2012/0156712 A1* | 6/2012 | Takats | H01J 49/165 435/29 |
| 2012/0201846 A1 | 8/2012 | Rehm et al. | |
| 2012/0295276 A1 | 11/2012 | Cooks et al. | |
| 2012/0308555 A1 | 12/2012 | Polakiewicz et al. | |
| 2013/0123919 A1 | 5/2013 | Goldstein et al. | |
| 2013/0178845 A1* | 7/2013 | Smith | A61B 18/1492 606/33 |
| 2013/0181126 A1 | 7/2013 | Jong | |
| 2013/0303846 A1* | 11/2013 | Cybulski | A61B 1/0684 600/104 |
| 2014/0039480 A1* | 2/2014 | Van Wyk | A61B 18/148 606/33 |
| 2014/0151547 A1* | 6/2014 | Bajic | H01J 49/26 250/282 |
| 2014/0268134 A1 | 9/2014 | O'Connor | |
| 2014/0276775 A1 | 9/2014 | Funk et al. | |
| 2014/0291506 A1 | 10/2014 | Tikhonski et al. | |
| 2014/0297201 A1 | 10/2014 | Knorr et al. | |
| 2014/0299577 A1 | 10/2014 | Chung et al. | |
| 2014/0303449 A1* | 10/2014 | Balog | A61B 18/1402 600/249 |
| 2014/0326865 A1* | 11/2014 | Pringle | H01J 49/06 250/282 |
| 2014/0336456 A1* | 11/2014 | Demers | A61B 10/04 600/106 |
| 2014/0353488 A1* | 12/2014 | Takats | G01N 27/622 250/282 |
| 2014/0353489 A1* | 12/2014 | Szalay | H01J 49/16 250/282 |
| 2015/0021469 A1 | 1/2015 | Bajic | |
| 2015/0048255 A1 | 2/2015 | Jarrell | |
| 2015/0087003 A1 | 3/2015 | Charles et al. | |
| 2015/0144782 A1 | 5/2015 | Fogwill et al. | |
| 2015/0192590 A1 | 7/2015 | Sodeoka et al. | |
| 2015/0201913 A1 | 7/2015 | Takats | |
| 2015/0340215 A1* | 11/2015 | Pringle | H01J 49/0459 250/282 |
| 2016/0002696 A1 | 1/2016 | Galiano | |
| 2016/0133450 A1 | 5/2016 | Green et al. | |
| 2016/0215322 A1 | 7/2016 | Goodlett et al. | |
| 2016/0247668 A1* | 8/2016 | Szalay | H01J 49/14 |
| 2016/0341712 A1* | 11/2016 | Agar | G01N 33/57496 |
| 2016/0372313 A1 | 12/2016 | Brown et al. | |
| 2017/0103880 A1 | 4/2017 | Syage | |
| 2018/0047551 A1* | 2/2018 | Jones | H01J 49/0409 |
| 2018/0047555 A1* | 2/2018 | Pringle | A61B 5/0075 |
| 2018/0053644 A1* | 2/2018 | Jones | A61F 13/38 |
| 2018/0136091 A1 | 5/2018 | Ryan et al. | |
| 2018/0254177 A1* | 9/2018 | Gao | H01J 49/161 |
| 2018/0256239 A1* | 9/2018 | Johnson | A61B 18/042 |

FOREIGN PATENT DOCUMENTS

| | | | |
|---|---|---|---|
| CA | 2882003 A1 | 2/2014 | |
| CN | 101073137 A | 11/2007 | |
| CN | 101170043 A | 4/2008 | |
| CN | 101178381 A | 5/2008 | |
| CN | 101223625 A | 7/2008 | |
| CN | 101288146 A | 10/2008 | |
| CN | 101372502 A | 2/2009 | |
| CN | 101413905 A | 4/2009 | |
| CN | 101490524 A | 7/2009 | |
| CN | 201266145 Y | 7/2009 | |
| CN | 101657158 A | 2/2010 | |
| CN | 101819179 A | 9/2010 | |
| CN | 101871914 A | 10/2010 | |
| CN | 102026709 A | 4/2011 | |
| CN | 102121921 A | 7/2011 | |
| CN | 102137618 A | 7/2011 | |
| CN | 102164675 A | 8/2011 | |
| CN | 102264404 A | 11/2011 | |
| CN | 102367424 A | 3/2012 | |
| CN | 102445544 A | 5/2012 | |
| CN | 102483369 A | 5/2012 | |
| CN | 102800553 A | 11/2012 | |
| CN | 102879453 A | 1/2013 | |
| CN | 102924993 A | 2/2013 | |
| CN | 102928610 A | 2/2013 | |
| CN | 103295873 A | 9/2013 | |
| CN | 103335984 A | 10/2013 | |
| CN | 103597574 A | 2/2014 | |
| CN | 103748233 A | 4/2014 | |
| CN | 104062348 A | 9/2014 | |
| CN | 104254772 A | 12/2014 | |
| CN | 104254901 A | 12/2014 | |
| CN | 104284984 A | 1/2015 | |
| CN | 104582616 A | 4/2015 | |
| EP | 0437358 A2 | 7/1991 | |
| EP | 1855306 A1 | 11/2007 | |
| EP | 0169469 | 7/2009 | |
| EP | 1730519 B1 | 7/2010 | |
| EP | 3265817 A1 | 1/2018 | |
| EP | 3266035 A1 | 1/2018 | |
| EP | 3265818 B1 | 2/2020 | |
| GB | 2420008 A | 5/2006 | |
| GB | 2425178 A | 10/2006 | |
| GB | 2491486 A | 12/2012 | |
| JP | S63243864 A | 10/1988 | |
| JP | 03001435 A | 1/1991 | |
| JP | H0785834 A | 3/1995 | |
| JP | H07130325 A | 5/1995 | |
| JP | H10247472 A | 9/1998 | |
| JP | 10302710 A | 11/1998 | |
| JP | H1164283 A | 3/1999 | |
| JP | 2000097913 A | 4/2000 | |
| JP | 2000180413 A | 6/2000 | |
| JP | 2001183345 A | 7/2001 | |
| JP | 2002170518 A | 6/2002 | |
| JP | 2004264043 A | 9/2004 | |
| JP | 2005205181 A | 8/2005 | |
| JP | 2006329710 A | 12/2006 | |
| JP | 2007051934 A | 3/2007 | |
| JP | 2007170870 A | 7/2007 | |
| JP | 2007218916 A | 8/2007 | |
| JP | 2010169454 A | 8/2010 | |
| JP | 2014515831 A | 7/2014 | |
| JP | 2015503109 A | 1/2015 | |
| JP | 2015504160 A | 2/2015 | |
| KR | 1020100106336 A | 10/1988 | |
| KR | 1020020013544 | 9/1998 | |
| WO | 9734534 A1 | 9/1997 | |
| WO | 0160265 A1 | 8/2001 | |
| WO | 2008148557 A2 | 12/2008 | |
| WO | 2010075265 A2 | 7/2010 | |
| WO | 2010136887 A1 | 12/2010 | |
| WO | 2011114902 A1 | 9/2011 | |
| WO | 2012143737 A1 | 10/2012 | |
| WO | 2012174437 A1 | 12/2012 | |
| WO | WO-2012164312 A2 * | 12/2012 | ......... H01J 49/0459 |
| WO | 2013098645 A2 | 7/2013 | |
| WO | 2013102670 A1 | 7/2013 | |
| WO | WO-2013098642 A2 * | 7/2013 | ............ H01J 49/16 |
| WO | 2013/148162 | 10/2013 | |
| WO | 2014106165 A1 | 7/2014 | |
| WO | 2014128629 A1 | 8/2014 | |
| WO | 2014140601 A1 | 9/2014 | |
| WO | 2014142926 A1 | 9/2014 | |
| WO | 2014202828 A1 | 12/2014 | |
| WO | 2015004457 A1 | 1/2015 | |

(56) References Cited

FOREIGN PATENT DOCUMENTS

| WO | 2015132579 A1 | 9/2015 |
|---|---|---|
| WO | 2016046748 A1 | 3/2016 |
| WO | 2016142674 A1 | 9/2016 |
| WO | 2016156615 A1 | 10/2016 |

OTHER PUBLICATIONS

Agar, Nathalie et al., "Development of Stereotactic Mass Spectrometry for Brain Tumor Surgery", Biosis, Neurosurgery Online, vol. 68, No. 2, (2011).
Ahlf, Dorothy R. et al., "Correlated Mass Spectrometry Imaging and Confocal Raman Microscopy for Studies of Three-Dimensional Cell Culture Sections", Analyst, vol. 139, No. 18, pp. 4578 (2014).
Azimzadeh, Omid et al., "Formalin-Fixed Paraffin-Embedded (FFPE) Proteome Analysis Using Gel-Free and Gel-Based Proteomics", Journal of Proteome Research, vol. 9, No. 9, pp. 4710-4720 (2010).
Balgley, Brian M. et al., "Evaluation of Archival Time on Shotgun Proteomics of Formalin-Fixed and Paraffin-Embedded Tissues", Journal of Proteome Research, vol. 8, No. 2, pp. 917-925 (2009).
Balog, Julia et al., "Identification of Biological Tissues by Rapid Evaporative Ionization Mass Spectrometry", Analytical Chemistry, vol. 82, No. 17, pp. 7343-7350 (2010).
Balog, Julia et al., "Supporting Information for Identification of Biological Tissues by Rapid Evaporative Ionization Mass Spectrometry", pp. S1-S9, http://pubs.acs.org/doi/suppl/10.1021/ac101, (2013).
Balog, J. et al., "Intraoperative Tissue Identification Using Rapid Evaporative Ionization Mass Spectrometry", Science Translational Medicine, vol. 5, No. 194, pp. 194ra93 (2013).
Balog, J. et al., "Supplementary Materials: Intraoperative Tissue Identification Using Rapid Evaporative Ionization Mass Spectrometry", Science Translational Medicine, vol. 5, No. 194, pp. 194ra93 (2013).
Bean, Heather D. et al., "Bacterial Volatile Discovery Using Solid Phase Microextraction and Comprehensive Two-Dimensional Gas Chromatographytime-of-Flight Mass Spectrometry", Journal of Chromatography B, vol. 901, pp. 41-46 (2012).
Bellet, V. et al., "Proteomic Analysis of RCL2 Paraffin-Embedded Tissues", Journal of Cellular and Molecular Medicine, vol. 12, No. 5B, pp. 2027-2036 (2008).
Bocklitz, T.W. et al., "Deeper Understanding of Biological Tissue: Quantitative Correlation of MALDI-Tof and Raman Imaging", Analytical Chemistry, vol. 85, No. 22, pp. 10829-10834 (2013).
Cole, Laura M. et al., "Mass Spectrometry Imaging for the Proteomic Study of Clinical Tissue", Proteomics-Clinical Applications, vol. 9, No. 3-4, pp. 335-341 (2015).
Cselik, Z. et al., "Impact of Infrared Laser Light-Induced Ablation at Different Wavelengths on Bovine Intervertebral Disc Ex Vivo: Evaluation with Magnetic Resonance Imaging and Histology", Lasers in Surgery and Medicine, vol. 44, No. 5, pp. 406-412 (2012).
Davies, T.J. et al., "Volatile Products from Acetylcholine as Markers in the Rapid Urine Test Using Head-Space Gas-Liquid Chromatography B: Biomedical Sciences and Applications", Journal of Chromatography, vol. 307, pp. 11-21 (1984).
European Commission, "ISD Report Summary", http://cordis.europa.eu/result/rcn/163435_e, (2016).
Fahy, Eoin, et al., "Lipid Classification, Structures and Tools", Biochimica at Biophysica Acta (BBA)—Molecular and Cell Biology of Lipids, vol. 1811, No. 11, pp. 637-647 (2011).
Gerbig, Stefanie et al., "Analysis of Colorectal Adenocarcinoma Tissue by Desorption Electrospray Ionization Mass Spectrometric Imaging", Analytical and Bioanalytical Chemistry, vol. 403, No. 8, pp. 2315-2325 (2012).
Golf, Ottmar et al., "Rapid Evaporative Ionization Mass Spectrometry Imaging Platform for Direct Mapping from Bulk Tissue and Bacterial Growth Media", Analytical Chemistry, vol. 87, No. 5, pp. 2527-2534 (2015).
Golf, Ottmar et al., "XMS: Cross-Platform Normalization Method for Multimodal Mass Spectrometric Tissue Profiling", Journal of the American Society for Mass Spectrometry, vol. 26, No. 1, pp. 44-54 (2014).
Guenther, Sabine et al., "Electrospray Post-Ionization Mass Spectrometry of Electrosurgical Aerosols", Journal of the American Society for Mass Spectrometry, vol. 22, No. 11, pp. 2082-2089 (2011).
Hobbs, S.K. et al., "Magnetic Resonance Image-Guided Proteomics of Human Glioblastoma Multiforme", Journal of Magnetic Resonance Imaging, vol. 18, pp. 530-536 (2003).
Hsu, Cheng-Chih et al., "Visualizing Life with Ambient Mass Spectrometry", Current Opinion in Biotechnology, vol. 31, pp. 24-34 (2015).
Jadoul, L. et al., "Matrix-Assisted Laser Desorption/Ionization Mass Spectrometry and Raman Spectroscopy: An Interesting Complementary Approach for Lipid Detection in Biological Tissues", European Journal of Lipid Science and Technology. vol. 116, No. 8, pp. 1080-1086 (2014).
Jain, M. et al., "Metabolite Profiling Identifies a Key Role for Glycine in Rapid Cancer Cell Proliferation", American Association for the Advancement of Science, vol. 336, No. 6084, pp. 1040-1044 (2012).
Jarmusch, Alan K et al., "Detection of Strep Throat Causing Bacterium Directly from Medical Swabs by Touch Spray-Mass Spectrometry", Analyst, vol. 139, No. 19, pp. 4785 (2014).
Jarmusch, Alan K. et al., "Supplemental Information Detection of Strep Throat Causing Bacterium Directly from Medical Swabs by Touch Spray-Mass Spectrometry", http://www.rsc.org/suppdata/an/c4/c4an00959 (2016).
Lazova, Rossitza et al., "Imaging Mass Spectrometry-A New and Promising Method to Differentiate Spitz Nevi From Spitzoid Malignant Melanomas", American Journal of Dermatopathology, vol. 34, No. 1, pp. 82-90 (2012).
Li, Yan et al., "Aberrant Mucin5B Expression in Lung Adenocarcinomas Detected by iTRAQ Labeling Quantitative Proteomics and Immunohistochemistry", Clinical Proteomics, vol. 10, No. 1, pp. 15 (2013).
Luge, S. et al., "Use of a Lower Power, High Frequency Stabilized Capacitive Plasma Combined with Graphite Furnace Vaporization for the Atomic Emission Spectrometric Analysis of Serum Samples", Analytical Chimica Acta, vol. 332, No. 2-3, pp. 193-199 (1996).
Mccullough, Bryan J. et al., "On-Line Reaction Monitoring by Extractive Electrospray Ionisation", Rapid Communications in Mass Spectrometry, vol. 25, No. 10, pp. 1445-1451 (2011).
Murray, Patrick R, "What Is New in Clinical Microbiology-Microbial Identification by MALDI-TOF Mass Spectrometry", Journal of Molecular Diagnostics, vol. 14, No. 5, pp. 419-423 (2012).
Nicholson, Jeremy K. et al., "Metabolic Phenotyping in Clinical and Surgical Environments", Nature, vol. 491, No. 7424 pp. 384-392 (2012).
Plata, N. et al., "Aerosols Sampling Using a New Cryogenic Instrument", Journal of Aerosol Science, vol. 37, No. 12, pp. 1871-1875 (2006).
Rodriguez-Rigueiro, Teresa et al., "A Novel Procedure for Protein Extraction from Formalin-Fixed Paraffin-Embedded Tissues", Proteomics, vol. 11, No. 12, pp. 2555-2559 (2011).
Schafer, Karl-Christian et al., "In Vivo, In Situ Tissue Analysis Using Rapid Evaporative Ionization Mass Spectrometry", Angewandte Chemie International, vol. 48, No. 44, pp. 8240-8242 (2009).
Shoemaker, Robert H., "The NCI60 Human Tumour Cell Line Anticancer Drug Screen", (2013).
Strittmatter, N. et al., "Anaylsis of Intact Bacteria Using Rapid Evaporative Ionisation Mass Spectrometry", Chemical Communications, vol. 49, No. 55, pp. 6188 (2013).
Strittmatter, N. et al., "Characterization and Identification of Clinically Relevant Microorganisms Using Rapid Evaporative Ionization Mass Spectrometry", Analytical Chemistry, vol. 86, No. 13, pp. 6555-6562 (2014).
Uribe, D.O. et al., "Piezoelectric Self-Sensing System for Tactile Intraoperative Brain Tumor Delineation in Neurosurgery", Proceedings of the 31st Annual International Conference of the IEEE

(56) References Cited

OTHER PUBLICATIONS

Engineering in Medicine and Biology Society: Engineering the Future of BioMedicine, pp. 737-740 (2009).
Vander Wilp, W. et al., "*Lead in Micro-Samples of Whole Blood by Rhenium-Cup in-Torch Vaporization-Inductively Coupled Plasma-Atomic Emission Spectrometry (ITV-ICP-AES)*", Fresenius' Journal of Analytical Chemistry, vol. 368, No. 7, pp. 734-736 (2000).
Vircks, Kyle E. et al., "*Rapid Screening of Synthetic Cathinones as Trace Residues and in Authentic Seizures Using a Portable Mass Spectrometer Equipped with Desorption Electrospray Ionization*", Rapid Communications in Mass Spectrometry, vol. 26, No. 23, pp. 2665-2672 (2012).
Summons to Attend Oral Proceedings Pursuant to Rule 115(1) EPC of EP Application No. 12726643.5, dated Apr. 20, 2018, 7 pages.
Chen et al., "Surface desorption atmospheric pressure chemical ionization mass spectrometry for direct ambient sample analysis without toxic chemical contamination", Journal of Mass Spectrometry, 42(8):1045-1056, Jan. 1, 2007.
Chen, H., et al: "Neutral desorption sampling coupled to extractive electrospray ionization mass spectrometry for rapid differentiation of biosamples by metabolomic fingerprinting", Journal of Mass Spectromety, vol. 42, No. 9, Sep. 1, 2007 pp. 1123-1135.
Crawshaw, Benjamin et al., "Gastrointestinal Surgery: Real-Time Tissue Identification During Surgery", Nature Review/Gastroenterology & Hepatology , vol. 10, No. 11. pp. 624-625 (Sep. 2013).
Gustafsson, Ove J.R. et al., "Proteomic Developments in the Analysis of Formalin-Fixed Tissue", Biochimica et Biophysica Acta, vol. 1854, No. 6, pp. 559-580.
Hensman C., et al: "Chemical Composition of Smoke Produced by High-Frequency Electrosurgery in a Closed Gaseous Environment an in Vitro Study", Surgical Endoscopy, vol. 12, No. 8, Aug. 1, 1998 (Aug. 1, 1998), pp. 1017-1019.
Lieuwe, D.J. et al., "Volatile Metabolites of Pathogens: A Systematic Review", PLoS Pathogens, vol. 9, Issue 5, e1003311 (May 2013) whole document.
Moot, A. et al: "Composition of Volatile Organic Compouds in Diathermy Plume as Detected by Selected Ion Flow Tube Mass Spectrometry", ANZ Journal of Surgery, vol. 77, No. 1-2, (Jan. 2007) pp. 20-23.
Pirro, Valentina et al., "Direct Drug Analysis from Oral Fluid Using Medical Swab Touch Spray Mass Spectrometry", Analytica Chimica Acta, vol. 861, Jan. 7, 2015 pp. 47-54.
Ellis, S. et al., "Surface Analysis of Lipids by Mass Spectrometry: More Than Just Imaging", Progress in Lipid Research Pergamon Press, vol. 52, No. 4, pp. 329-353 (Oct. 2013).
Strittmatter, N. et al., "Taxon-Specific Markers for the Qualitative and Quantitative Detection of Bacteria in Human Samples", https://www.msacl.org/2015 US Long Abstract.
Strittmatter, N.: "Home—Miss Nicole Strittmatter" Retrieved from the Internet URL: http://www.imperial.ac.uk/people/n.strittmatter12 [retrieved on May 19, 2016] the whole document.
Tait, Emma et al., "Identification of Volatile Organic Compounds Produced by Bacteria Using HS-SPME-GC-MS", Journal of Chromatographic Sci, pp. 1-11.
Wehofsky, et al ("Automated deconvolution and deisotoping of electrospray mass spectra" J. Mass Spectrom. 2002; 37: pp. 223-229).
Al Sahaf et al., "Chemical Composition of Smoke Produced by High-Frequency Electrosurgery", Irish Journal of Medical Science, vol. 176, No. 3, pp. 229-232, 2007.
Boughton, B. et al., "Mass spectrometry imaging for plant biology: a review", Phytochemistry Reviews, 15(3):445-488 (2015).
Barrett et al., "Surgical Smoke: A Review of the Literature", Surgical Endoscopy, vol. 17, No. 6, pp. 979-987, 2003.
Down, "A DESI-Rable Ionization Revolutionizes Mass Spectrometry", Base Peak, 2005.
International Search Report and Written Opinion for International Application. No. PCT/IB2012/003009, dated Aug. 14, 2013, 17 pages.
PCT International Search Report and Written Opinion for International Appln. No. PCT/IB2010/001261, dated Sep. 21, 2010, 5 pages.
PCT International Search Report and Written Opinion for International Appln. No. PCT/IB2012/002995, dated Sep. 10, 2013, 3 pages.
Qiao et al., "Electrostatic-Spray Ionization Mass Spectrometry", Analytical Chemistry, vol. 84, No. 17, pp. 7422-7430, 2012.
Lee et al., "Thermally Assisted Electrospray Interface for Liquid Chromatography/Mass Spectrometry", Rapid Communications in Mass Spectrometry, vol. 6, pp. 727-733, 1992.
McEwen et al., "Analysis of Solids, Liquids, and Biological Tissues Using Solids Probe Introduction at Atmospheric Pressure on Commercial LC/MS Instruments", Anal. Chem., vol. 77, pp. 7826-7831, 2005.
Sakairi et al., "Characteristics of a Liquid Chromatograph/Atmospheric Pressure Ionization Mass Spectrometer", Anal. Chem., vol. 60, pp. 774-780, 1988.
Takats et al., "Characterization of DESI-FTICR Mass Spectrometry—From ECD to Accurate Mass Tissue Analysis", Journal of Mass Spectrometry, vol. 43, pp. 196-203, 2008.
Slemr et al., Concentration Profiles of Diamines in Fresh and aerobically Stored Park and Beef, American Chemical Society, 1985.
Eagles, et al., "Fast Atom Bombardment Mass Spectrometry of Amine Mixtures", John Wiley & Sons, Ltd, 1988.
Mulligan, Christopher C. et al., "Desorption electrospray ionization with a portable mass spectrometer: in situ analysis of ambient surfaces", Chemical Communications—Chemcom, No. 16, pp. 1709-1711, (Jan. 2006).
Van Berkel, "Thin-Layer Chromatography and El3ectrospray Mass Spectrometry Coupled Using a Surface Sampling probe". Anal. Chem. 2002.
Takats et al., "Mass Spectrometry Sampling Under Ambient Conditions with Desorption Electrospray Ionization", Science, vol. 306, 2004.
Tottszer et al., "Laser Heating Versus Resistive Heating in the Field-Desorption Mass Spectrometry of Organic Polymers", J. Phys. D: Appl. Phys., vol. 21, pp. 1713-1720, 1988.
Zhou X. et al., "Development of miniature mass spectrometry systems for bioanalysis outside the conventional laboratories." Bioanalysis, 6 (11) 1497-1508 (2014).
Bolt, F., et al., "Automated High-Throughput Identification and Characterization of Clinically Important Bacteria and Fungi using Rapid Evaporative Ionization Mass Spectrometry," American Chemical Socieity, 88 9419-9426 (2016).
McJimpsey, E.L., et al., "Parameters Contributing to Efficient Ion Generation in Aerosol MALDI Mass Spectrometry," American Society for Mass Spectrometry pp. 1044-0305 (2007).
Mutters, N.T., et al., "Performance of Kiestra Total Laboratory Automation Combined with MS in Clinical Microbiology Practice," Annals of Laboratory Medicine 34: 111-117 (2014).
Longuespée, R., et al., Tissue Proteomics for the Next Decade? Towards a Molecular Dimension in Histology, OMICS a Journal of Integrative Biology 28(9): 539-552 (2014).
Nielen, M et al., "Desorption electrospray ionization mass spectrometry in the analysis of chemical food contaminants in food", Trac Trends in Analytical Chemistry, 30(2):165-180 (2011).
Lu, K., et al., "Arsenic Exposure Perturbs the Gut Microbiome and its Metabolic Profile in Mice: An Integrated Metagenomics and Metabolomics Analysis," Environmental Health Perspectives, 122(3): 284-291 (2014).
Suarez, S., et al., Ribosomal proteins as biomarkers for bacterial identification by mass spectrometry in the clinical microbiology laboratory, Journal of microbiological Methods, 94: 390-396 (2013).
Trimpin, S. et al., New Ionization Method for Analysis on Atmospheric Pressure Ionization Mass Spectrometers Requiring Only Vacuum and Matrix Assistance, Analytical Chemistry, 85:2005-2009 (2013).
Cha, S., Laser desorption/ionization mass spectrometry for direct profiling and imaging of small moledcules from raw biological materials, Doctoral Dissertation, Iowa State University (2008).

(56) References Cited

OTHER PUBLICATIONS

Asano et al., "Self-aspirating atmospheric pressure chemical ionization source for direct sampling of analytes on Surfaces in liquid solution", Rapid Communications in Mass Spectrometry 2005.
International Search Report and Written Opinion for application No. PCT/GB2017/051050, dated Jun. 27, 2017, 15 pages.
Gerbig, Stefanie et al, "Spatially resolved investigation of systemic and contact pesticides in plant material by desorption electrospray ionization mass spectrometry imagine", Analytical and Bioanalytical Chemistry, 407 (24):7379-7389 (2015).
Lesiak, esiak A. et al., "Rapid detection by direct analysis in real time-mass spectrometry (DART-MS) of psychoactive plant drugs of abuse: the case of Mitragyna speciosa aka "Kratom"", 242:210-218 (2014).
Bartels, B. et al., "Spatially resolved in vivo plant metabolomics by laser ablation-based mass spectrometry imaging (MSI) techniques: LDI-MSI and LAESI", Frontiers in Plant Science vol. 6 (2015).
Na, et al., "Development of a Dielectric Barrier Discharge Ion Source for Ambient Mass Spectrometry", Journal of the American Society for Mass Spectrometry, Elsevier Science Inc, vol. 18, No. 10, pp. 1859-1862, Sep. 20, 2007.
Hsu, et al., "Microscopy ambient ionization top-down mass spectrometry reveals developmental patterning", Proceedings of the National Academy of Sciences, vol. 110, No. 37, pp. 14855-14860, Aug. 22, 2013.
International Search Report and Written Opinion for International Application No. PCT/GB2016/052956, dated Jan. 26, 2017, 16 pages.
Schäfer, K.C., et al., "In Situ, Real-Time Identification of Biological Tissue by Ultraviolet and Infrared Laser Desorption Ionization Mass Spectrometry", Analytical Chemistry, 83(5):1632-1640, Mar. 1, 2011.
Jackson, S. N. et al., "On-line laser desorption/ionization mass spectrometry of matrix-coated aerosols, Rapid Communications in Mass Spectrometry," vol. 18, pp. 2041-2045 (2004).
Dong, Y., et al., "Sample Preparation for Mass Spectrometry Imaging of Plant Tissues: A Review", Frontiers in Plant Science 7(60): 1-16 (2016).
Communication pursuant to Article 94(3) EPC, for application No. 16710788.7, dated Jun. 13, 2019, 9 pages.
Examination Report under Section 18(3), for application No. GB1714122.7, dated May 9, 2019, 6 pages.
Bagley, B.M. et al. "Evaluation of archival time on shotgun proteomics of formalin-fixed and paraffin-embedded tissues", Journal of Proteome Research 8(2):917-925, (2009).
Cho, YT., et al. "Differentiation of Virulence of Helicobacter Pyloriby Matrix-Assited Laser Desorption/Ionization Mass Spectrometry and Multivariate Analyses" Clinica Chimica ACTA, Elsevier BV, 424:123-130, May 26, 2013.
Kohler, M. et al. "Characterization of lipid extracts from brain tissue and tumors using Raman spectroscopy and mass spectrometry," Anal Bioana Chem, 393:1513-1520, Jan. 20, 2009.
Harry, K. H., et al. "Effect of protein coating of flocked swabs on the collection and release of clinically important bacteria", Indian Journal of Medical Microbiology, 32(3):301-303 (2014).
Blais, B. W., "Swab-Based Enzyme Immunoassay System for Detection of Meat Residues on Food Contact Surfaces as a Hygiene Monitoring Tool", Journal of Food Protection, 62(4):386-389 (1999).
Farhat, S. E., et al., "Efficacy of a Swab Transport System in Maintaining Viability of *Neisseria gonorrhoeae* and *Streptococcus pneumoniae*", Journal of Clinical Microbiology, 39(8):2958-2960 (2001).
Hachmoeller et al., "Element bioimaging of liver needle biopsy specimens from patients with Wilsons disease by laser ablation-inductively coupled plasma-mass spectrometry", Journal of Trace Elements in Medicine and Biology, 35:97-102, Feb. 10, 2016.
Guenther et al., "Spatially Resolved Metabolic Phenotyping of Breast Cancer by Desorption Electrospray Ionization Mass Spectrometry", Cancer Research, 75:1828-1837, Feb. 17, 2015.

Extended EP Search Report for EP Patent Application No. 19171058.1, dated Nov. 15, 2019.
Santagata, S., et al., "Intraoperative mass spectrometry mapping of an onco-metabolite to guide brain tumor surgery", Proceedings of the National Academy of Sciences (PNAS), 111(30):11121-11126, Jun. 30, 2014.
Chipuk, J. E., et al., "Transmission Mode Desorption Electrospray Ionization", Journal of the American Society for Mass Spectrometry, 19(11):1612-1620, Nov. 1, 2008.
Harry, E. L. et al., "Direct analysis of pharmaceutical formulations from non-bonded reversed-phase thin-layer chromatography plates by desorption electrospray ionisation ion mobility mass spectrometry", Rapid Communications in Mass Spectrometry, 23(17):2597-2604, Jul. 28, 2009.
Chen, H., et al., "What Can We Learn from Ambient Ionization Techniques", Journal of the American Society for Mass Spectrometry, 20:1947-1963, (2009).
Sankaranarayanan, G., et al., "Common Uses and Cited Complications of Energy in Surgery", Surg Endosc., 27:3056-3072, (2013).
Rau, H.G., et al., "The use of water-jet dissection in open and laparoscopic liver resection", HPB, 10: 275280, (2008).
Chen et al. "Desorption Electrospray Ionization Mass spectrometry for high-thoughput analysis of Pharamaceutical samples in the ambient environment" (Year: 2005).
Office Action for CN Patent Application No. 201680025801.0 dated Apr. 7, 2020.
Office Action for CN Patent Application No. 201680025801.0 dated Apr. 7, 2020 translation.
Adams, F., et al, "Inorganic Mass Spectrometry", copyright John Wiley Sons, Inc. pp. 174-180 (1988).
Vemury, S., and Pratsinis, S.E., "Charging and Coagulation During Flame Synthesis of Silica", Journal of Science Aerosol 27(6):951-966 (1996).
Examination Report under Section 18(3), for application No. GB1715787.6, dated Jun. 1, 2020, 6 pages.
CNOA for application No. 201680026285.3 dated Jun. 12, 2020, 12 pages.
Panpradist, N., et al., "Swab Sample Transfer for Point-Of-Care Diagnostics: Characterization of Swab types and Manual Agitation Methods", Plos One 9(9):1-11 (2014).
Partial European Search Report for EP20181905.9, dated Aug. 27, 2020, 14 pages.
Roddy, T., et al., "Imaging of Freeze-Fractured Cells with in Situ Fluorescence and Time-of-Flight Secondary Ion Mass Spectrometry", Analytical Chemistry 74(16):4011-4019 (2002).
Petrotchenko, E.V., et al., "Combining Fluorescence Detection and Mass Spectrometric Analysis for Comprehensive and Quantitative Analysis of Redox-Sensitive Cysteines in Native Membrane Proteins", Analytical Chemistry 78 (23):7959-7966 (2006).
Ablonczy, Z., et al., "The utilization of fluorescence to identify the components of lipofuscin by imaging mass spectrometry", Proteomics 14(7-8):936-944 (2014).
Enthaler, B., et al., "Improved sample preparation for MALDI-MSI of endogenous compounds in skin tissue sections and mapping of exogenous active compounds subsequent to ex-vivo skin penetration" Anal Bioanal Chem 402:1159-1167 (2012).
Extended EP search report for EP Application No. 20172634.6, dated Sep. 14, 2020, 8 pages.
Office Action for application No. CN201680025801.0 dated Oct. 12, 2020 original document and translation.
Adams, F., et al., "Inorganic Mass Spectrometry", (1993) Abstract.
Dong, Y.M.B.A., "Polymer Analysis Handbook", China Petrochemical Press (2004) 8 pages.
Waters DESI System Operator's Guide 715004701/Revision A, Waters Corporation, [online] Jan. 2015 [retrieved on Dec. 3, 2020]. Retrieved from Internet URL: https://www.waters.com/webassets/cms/support/docs/715004701ra.pdf. 141 pages.
Shin, Y-S., et al., "Desorption Electrospray Ionization-Mass Spectrometry of Proteins" Analytical Chemistry 79:3514-3518 (2007).
Chen, X, ed., "Liquid Chromatography-Mass Spectrometry—Chapter 8", in Principle and Application of Chromatographic Analysis Technology, Chinese People's Public Security University Press, (Jan. 2014) 6 pages.

(56) References Cited

OTHER PUBLICATIONS

Song, Y., et al., "Rapid ambient mass spetrometric profiling of intact, untreated bacteria using desoprtion electrospray ionization" ChemComm pp. 61-63 (2007).

Wiseman, J.M. and Li, J.B., "Elution, Partial Separation, and Identification of Lipids Directly from Tissue Slices on Planar Chromatography Media by Desoprtion Electrospray Ionization Mass Spectrometry", Anal Chem 82:8866-8874 (2010).

Krouskop, T., et al., "Elastic moduli of breast and prostate tissues under compression" Ultrasonic Imaging 20:260-274 (1998).

Aberg, P., et al., "Skin Cancer Identification Using Multifrequency Electrical Impedance—A Potential Screening Tool", IEEE Transactions on Biomedical Engineering, 51(12): 2097-2102 (2004).

Search and Examination Report under Sections 17 and 18(3) for GB1715767.8, dated Nov. 26, 2020, 6 pages.

Examination Report under Section 18(3) for Application No: GB2015580.0, dated Jan. 21, 2021, 4 pages.

CNOA for Application No. 2021042302205710, dated Apr. 27, 2021, original 10 pp.

Cornett, D. S., et al, "A Novel Histology-directed Strategy for MALDI-MS Tissue Profiling That Improves Throughput and Cellular Specificity in Human Breast Cancer", American Society for Biochemistry and Molecular Biology, pp. 1975-1983 (2006).

Examination Report for GB Patent Application No. GB2015580.0, dated Mar. 12, 2021.

Examination Report under Section 18(3) for Application No. GB1714165.6, dated Mar. 22, 2021, 6 pages.

Examination Report under Section 18(3) for Application No. GB1715750.4 dated Mar. 22, 2021, 5 pages.

Extended European Search Report for Application No. 20210062.4, dated Mar. 9, 2021, 13 pages.

Fenselau, C.C., "Rapid Characterization of Microorganisms by Mass Spectrometry—What Can Be Learned and How?" Journal of the American Society for Mass Spectrometry 24(8):1161-1166 (2013).

Forbes, T.P. et al., "Chemical imaging of artificial Fingerprints by desorption electro-flow focusing ionization mass spectrometry" Analyst 139(12):2982-2985 (2014).

Hillenkamp, F, et al., "Matrix-Assisted Laser Desorption/Ionization Mass Spectrometry of Biopolymers", Anal Chem 63 (24): 1193A-1203A (1991). Abstract.

Hrabak, J., et al., "Matrix-Assisted Laser Desorption Ionizataion-Time of Flight (MALDITOF) Mass Spectrometry for Detection of Antibiotic Resistance Mechanisms: from Research to Routine Diagnosis", CMR Journal 26(1): 103-114 (2013).

Rath, C.M., et al., "Molecular Analysis of Model Gut Microbiotas by Imaging Mass Spectrometry and Nanodesorption dectrospray Ionization Reveals Dietary Metabolite Tranformations" Analytical Chemistry 84(21):9259-9267 (2012).

Uetrecht, C. et al., "Modern Biomolecular Mass Spectrometry and its Role in Studying Virus Structure, Dynamics and Assembly" Angewandte Chemie International Edition 50(36):8248-8262 (2011).

\* cited by examiner

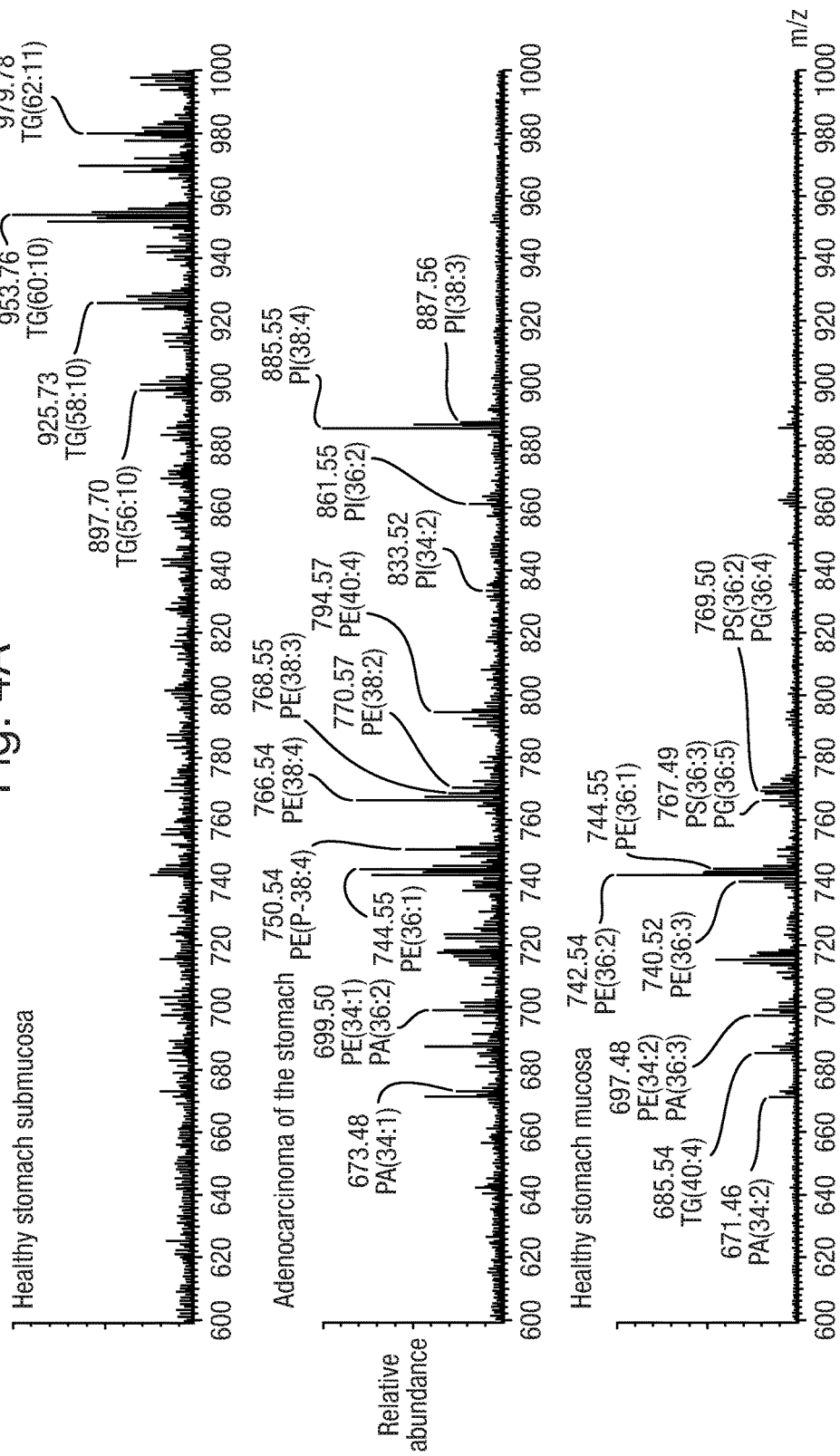

Version A:

Version B:

Version C:

IN VIVO ENDOSCOPIC TISSUE IDENTIFICATION TOOL

CROSS-REFERENCE TO RELATED APPLICATIONS

This application represents the U.S. National Phase of International Application number PCT/GB2016/050623 entitled "In Vivo Endoscopic Tissue Identification Tool" filed 7 Mar. 2016, which claims priority from and the benefit of United Kingdom patent application No. 1503876.3 filed on 6 Mar. 2015, United Kingdom patent application No. 1503864.9 filed on 6 Mar. 2015, United Kingdom patent application No. 1518369.2 filed on 16 Oct. 2015, United Kingdom patent application No. 1503877.1 filed on 6 Mar. 2015, United Kingdom patent application No. 1503867.2 filed on 6 Mar. 2015, United Kingdom patent application No. 1503863.1 filed on 6 Mar. 2015, United Kingdom patent application No. 1503878.9 filed on 6 Mar. 2015, United Kingdom patent application No. 1503879.7 filed on 6 Mar. 2015 and United Kingdom patent application No. 1516003.9 filed on 9 Sep. 2015. The entire contents of these applications are incorporated herein by reference.

FIELD OF THE INVENTION

The present invention relates generally to the analysis of a target (which may, for example, comprise in vivo, ex vivo or in vitro tissue) by ambient ionisation techniques such as rapid evaporative ionisation mass spectrometry ("REIMS"), and in particular to mass spectrometry and methods of mass spectrometry employing ambient ion sources, apparatus for performing rapid evaporative ionisation mass spectrometry, mass spectrometers, methods of electrosurgery and electrosurgical apparatus. Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/ or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

BACKGROUND

Rapid evaporative ionisation mass spectrometry ("REIMS") is a relatively new technique that is useful for the analysis of many different types of samples including the identification of tissue.

Reference is made to N. Strittmatter et al., Anal. Chem. 2014, 86, 6555-6562 which discloses an investigation into the suitability of using rapid evaporative ionisation mass spectrometry as a general identification system for bacteria and fungi.

The known approach for analysing bacterial colonies by rapid evaporative ionisation mass spectrometry involves using bipolar electrosurgical forceps and an electrosurgical RF generator. A bacterial colony is scraped from the surface of an agar layer using the bipolar electrosurgical forceps and a short burst of RF voltage from the electrosurgical RF generator is applied between the bipolar electrosurgical forceps. For example, it is known to apply 60 W of power in a bipolar mode at a frequency of 470 kHz sinusoid. The RF voltage which is applied to the electrosurgical forceps has the result of rapidly heating the particular portion of the bacterial colony which is being analysed due to its nonzero impedance. The rapid heating of the microbial mass results in an aerosol being generated. The aerosol is transferred directly into a mass spectrometer and the aerosol sample may then be analysed by the mass spectrometer. It is known to utilise multivariate statistical analysis in order to help distinguish and identify different samples.

Gastro-intestinal cancers are a leading cause of mortality and account for 23% of cancer-related deaths worldwide. In order to improve outcomes from these cancers, novel tissue characterisation methods are needed in order to facilitate accurate diagnosis.

Rapid evaporative ionization mass spectrometry ("REIMS") may be used for the real time identification of tissues e.g. during surgical interventions. Coupling of mass spectrometry with a surgical diathermy device has resulted in a sampling technology which has an intra-operative tissue identification accuracy of 92-100%.

This sampling technology allows surgeons to more efficiently resect tumours intra-operatively through minimizing the amount of healthy tissue removed whilst ensuring that all the cancerous tissue is removed.

Rapid evaporative ionisation mass spectrometry analysis of biological tissues has been shown to yield phospholipid profiles showing high histological and histopathological specificity—similar to Matrix Assisted Laser Desorption Ionisation ("MALDI"), Secondary Ion Mass Spectrometry ("SIMS") and Desorption Electrospray Ionisation ("DESI") imaging. A mass spectrometric signal is obtained by subjecting the cellular biomass to alternating electric current at radiofrequency which causes localized Joule-heating and the disruption of cells along with desorption of charged and neutral particles. The resulting aerosol or surgical smoke is then transported to a mass spectrometer for on-line mass spectrometric analysis.

It is desired to provide an improved method of inter alia identifying gastro-intestinal cancers.

SUMMARY

According to an aspect there is provided a method of analysis comprising:
providing a tool comprising a first device located within a tubing or a housing, wherein the tubing or the housing comprises a tool deployment opening and one or more separate aspiration ports;
using the first device to generate aerosol, smoke or vapour from one or more regions of a target; and
optionally obtaining chemical, physical, imaging, mass spectrometric, ion mobility or other data from the one or more regions of the target.

N. Strittmatter et al., Anal. Chem. 2014, 86, 6555-6562 does not disclose utilising an endoscopic tool having a housing with a tool deployment opening and one or more separate aspiration ports or fenestrations.

The various embodiments are particularly advantageous in that the provision of one or more aspiration ports (which are separate and distinct from the main tool deployment opening at the end of the tubing or housing) allows surgical smoke or aerosol to be aspirated into the tubing or housing and then to be passed to a mass spectrometer and/or ion mobility separator for analysis. This is advantageous since the main tool deployment opening at the end of the tubing or housing will tend to be blocked as the snare tightens (also at approximately the same time that a current may be applied to the snare) by e.g. a polyp which is being removed. It will be appreciated therefore that the aspiration ports are generally suitable for aspirating the aerosol, smoke or vapour generated from the target.

The surgical smoke or aspirated aerosol which is aspirated into the tubing or housing may then be directed into a vacuum chamber of the mass spectrometer and the surgical smoke or aspirated aerosol may then be ionised within the vacuum chamber of the mass spectrometer by colliding with a collision surface which may comprise a rapid evaporative ionisation mass spectrometry ionisation source. The rapid evaporative ionisation mass spectrometry ionisation source may further comprise a Venturi pump, a sampling capillary and ion optics which may be provided downstream of the collision surface.

According to an embodiment the collision surface may be heated.

The ion optics which may be provided immediately downstream of the collision surface may comprise a Step-Wave® ion guide. As will be understood by those skilled in the art, a StepWave® ion guide comprises two conjoined ion tunnel ion guides. Each ion guide comprises a plurality of ring or other electrodes wherein ions pass through the central aperture provided by the ring or other electrodes. Transient DC voltages or potentials are applied to the electrodes. The StepWave® ion guide is based on stacked ring ion guide technology and is designed to maximise ion transmission from the source to the mass analyser. The device allows for the active removal of neutral contaminants thereby providing an enhancement to overall signal to noise. The design enables the efficient capture of the diffuse ion cloud entering a first lower stage which is then may focused into an upper ion guide for transfer to the mass analyser.

The resulting analyte ions are then mass analysed and/or ion mobility analysed. As a result, a user of the tool or electrosurgical tool (e.g. a surgeon or a specialist nurse) can be provided with real time information concerning the nature of the tissue which is being resected. The various embodiments therefore allows a determination of the tissue type that is being resected and to help to ensure that all cancerous or potentially cancerous tissue has been removed and also helps to prevent an unnecessary amount of healthy tissue from being removed. The various embodiments are therefore able to play an important role in reducing the number of deaths due to gastro-intestinal cancer and to help prevent re-intervention due to incomplete excision of cancerous or potentially cancerous tissue.

The method (and apparatus) may generally find use in a surgical environment. However, it will be appreciated that the methods described herein may also generally comprise non-surgical, non-diagnostic and non-therapeutic methods.

The first device may comprise one or more electrodes.

Accordingly, any references herein to the first device should also be taken to apply in embodiments to one or more electrodes or one or more electrodes of the first device.

Similarly, the tool may generally comprise an electrosurgical tool and any references herein to the tool should also be taken to apply in embodiments to an electrosurgical tool.

The method may comprise method of rapid evaporative ionisation mass spectrometry or a method of ambient ionisation mass spectrometry.

According to an embodiment a rapid evaporative ionisation mass spectrometry ionization technique is provided which is integrated with an endoscopic polypectomy snare so as to allow in vivo analysis of the gastrointestinal tract.

According to an embodiment a rapid evaporative ionisation mass spectrometry endoscopic method is disclosed which has been tested in vivo.

A rapid evaporative ionisation mass spectrometry compatible endoscope according to an embodiment has been developed which has been shown to be capable of differentiating between healthy layers of the intestinal wall, cancer and adenomatous polyps based on the rapid evaporative ionisation mass spectrometry fingerprint of each tissue type in vivo.

The device is also capable of in-situ investigations of gut microbiota by the rapid evaporative ionisation mass spectrometry analysis of mucus and faecal residues.

From another aspect therefore there is provided a method of rapid evaporative ionisation mass spectrometry ("REIMS") comprising:

providing an electrosurgical tool comprising one or more electrodes located within a tubing or a housing, wherein the tubing or the housing comprises a tool deployment opening and one or more separate aspiration ports.

The one or more electrodes may comprise a snare.

The snare may comprise a polypectomy snare.

The one or more electrodes may comprise one or more hooks, one or more grabbers, one or more blades, one or more knives, one or more serrated blades, one or more probes, one or more biopsy tools, one or more robotic tools, one or more pincers, one or more electrosurgical pencils, one or more forceps, one or more bipolar forceps, one or more coagulation devices, one or more irrigation devices or one or more imaging tools.

The one or more electrodes may comprise a monopolar device.

A separate return electrode may also be provided.

The one or more electrodes may comprise: (i) a monopolar device, wherein the method optionally further comprises providing a separate return electrode; (ii) a bipolar device; or (iii) a multi phase RF device, wherein the method optionally further comprises providing a separate return electrode or electrodes.

According to an alternative embodiment, the one or more electrodes may comprise a bipolar device.

According to another embodiment the first device may comprise a pulsed plasma RF tool such as a PlasmaBlade® tool.

According to an embodiment the first device may comprise either: (i) an electrode, optionally a needle electrode, which is extendable from and/or retractable within the tubing or housing; or (ii) an optical fibre for directing laser radiation on to tissue or another surface, wherein the optical fibre is extendable from and/or retractable within the tubing or housing.

The method may further comprise initially deploying the tool or electrosurgical tool with the first device (e.g. the one or more electrodes or optical fibre) at least partially retracted within the tubing or the housing.

The method may further comprise deploying the first device (e.g. the one or more electrodes or optical fibre) so that the first device at least partially extends beyond the tool deployment opening.

The method may further comprise deploying the first device (e.g. the one or more electrodes or optical fibre) so that the first device contacts or otherwise interacts with tissue or other matter which is desired to be removed, resected or sampled.

The method may further comprise partially retracting the first device (e.g. the one or more electrodes or optical fibre) so that the first device captures or securely fastens around tissue or other matter which is desired to be removed, resected or sampled.

The method may further comprise providing an endoscope.

The endoscope may further comprise a light or an illumination device.

The method may further comprise deploying the tool or electrosurgical tool through a port in the endoscope.

The method may further comprise activating the tool or electrosurgical tool.

The step of activating the tool or electrosurgical tool may further comprise applying an RF voltage to the first device (e.g. the one or more electrodes).

The RF voltage may have an amplitude, a peak to peak voltage or a RMS voltage selected from the group consisting of: (i) about <100 V; (ii) about 100-200 V; (iii) about 200-300 V; (iv) about 300-400 V; (v) about 400-500 V; (vi) about 500-600 V; (vii) about 600-700 V; (viii) about 700-800 V; (ix) about 800-900 V; (x) about 900-1000 V; and (xi) about >1 kV.

The RF voltage may have a frequency selected from the group consisting of: (i) < about 1 kHz; (ii) about 1-2 kHz; (iii) about 2-3 kHz; (iv) about 3-4 kHz; (v) about 4-5 kHz; (vi) about 5-6 kHz; (vii) about 6-7 kHz; (viii) about 7-8 kHz; (ix) about 8-9 kHz; (x) about 9-10 kHz; (xi) about 10-20 kHz; (xii) about 20-30 kHz; (xiii) about 30-40 kHz; (xiv) about 40-50 kHz; (xv) about 50-60 kHz; (xvi) about 60-70 kHz; (xvii) about 70-80 kHz; (xviii) about 80-90 kHz; (xix) about 90-100 kHz; (xx) about 100-200 kHz; (xxi) about 200-300 kHz; (xxii) about 300-400 kHz; (xxiii) about 400-500 kHz; (xxiv) about 500-600 kHz; (xxv) about 600-700 kHz; (xxvi) about 700-800 kHz; (xxvii) about 800-900 kHz; (xxviii) about 900-1000 kHz; (xxix) about 1-2 MHz; and (xxx) about >2 MHz.

The one or more aspiration ports may be arranged in a regular pattern or in an irregular manner along the length of the tool or electrosurgical tool.

At least some of the aspiration ports may extend at least partially outwardly from the tubing or the housing.

At least some of the aspiration ports may be at least partially recessed within the tubing or the housing.

At least some of the aspiration ports may be arranged in rows wherein aspiration ports in a first row are staggered relative to aspiration ports in a second adjacent row.

The method may further comprise aspirating analyte, smoke, fumes, liquid, gas, surgical smoke, aerosol or vapour through the one or more aspiration ports.

The method may alternatively comprise aspirating the analyte, smoke, fumes, liquid, gas, surgical smoke, aerosol or vapour through the one or more aspiration ports in a substantially continuous manner.

According to an embodiment the method comprises aspirating the analyte, smoke, fumes, liquid, gas, surgical smoke, aerosol or vapour through the one or more aspiration ports in a substantially pulsed, discontinuous or irregular manner.

According to an embodiment the method may further comprise aspirating the analyte, smoke, fumes, liquid, gas, surgical smoke, aerosol or vapour through the one or more aspiration ports substantially only when an (e.g. electrosurgical cutting) applied voltage or potential is supplied to the tool or electrosurgical tool or the tool is otherwise energised.

The method may further comprise varying an aspiration duty cycle during the course of a surgical, non-surgical or other procedure.

The method may further comprise passing the analyte, smoke, fumes, liquid, gas, surgical smoke, aerosol or vapour into a vacuum chamber of a mass spectrometer. The aerosol, smoke or vapour generated from the target may be aspirated through the one or more aspiration ports and then transferred through at least a part of the tubing or housing towards the vacuum chamber of a mass spectrometer.

The method may further comprise causing at least some of the analyte, smoke, fumes, liquid, gas, surgical smoke, aerosol or vapour to impact upon a collision surface located within a vacuum chamber of the mass spectrometer wherein at least some of the analyte, smoke, fumes, liquid, gas, surgical smoke, aerosol or vapour is ionised upon impact with the collision surface in order to form analyte ions.

The method may further comprise heating the collision surface.

The step of heating the collision surface may comprise heating the collision surface to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The method may further comprise mass analysing the analyte ions.

The method may further comprise adding a matrix to the analyte, smoke, fumes, liquid, gas, surgical smoke, aerosol or vapour.

The matrix may added to the analyte, smoke, fumes, liquid, gas, surgical smoke, aerosol or vapour prior to the analyte, smoke, fumes, liquid, gas, surgical smoke, aerosol or vapour impacting upon the collision surface.

The matrix may selected from the group consisting of: (i) a solvent for the analyte, smoke, fumes, liquid, gas, surgical smoke, aerosol or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

The matrix may comprise a lockmass or calibration compound.

The method may further comprise providing real time and/or delayed information to a user of the tool or electrosurgical tool.

The information may comprise mass spectral information and/or tissue classification information.

The method may further comprise generating feedback and/or an alarm and/or an alert to a user of the tool or electrosurgical tool that tissue or other matter from an undesired target region or area is being mass analysed and/or ion mobility analysed.

The method may further comprise reducing or stopping electrical power to the tool or electrosurgical tool in the event that tissue or other matter from an undesired target region or area is being mass analysed and/or ion mobility analysed.

The method may further comprise generating feedback and/or an alarm and/or an alert to a user of the tool or electrosurgical tool that the tool or electrosurgical tool is operating in and/or is located in an undesired target region or area.

The method may further comprise reducing or stopping electrical power to the tool or electrosurgical tool in the event that the tool or electrosurgical tool is operating in and/or is located in an undesired target region or area.

For example, according to an embodiment a determination may be made that the tool or electrosurgical tool is cutting through a specific type of tissue such as muscle. In the case of a bowel operation a warning may be generated indicating that there is a potential danger of perforating the bowel.

The first device may generally comprise an ambient ion source. The method may comprise contacting or interacting with the one or more regions of the target under atmospheric or ambient conditions to generate the aerosol, smoke or vapour.

For instance, the first device may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electroflow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The first device may generally be arranged and adapted to generate aerosol, smoke or vapour from one or more regions of the target by direct evaporation or vaporisation of target material from the target by Joule heating or diathermy.

The target may comprise native or unmodified target material. That is, the target may comprise raw target material and/or the first device may interact directly with the target material without having to process the target material.

The native or unmodified target material may be unmodified by the addition of a matrix or reagent.

The first device may be arranged and adapted to generate aerosol, smoke or vapour from one or more regions of the target without the target requiring prior preparation.

The aerosol, smoke or vapour may comprise uncharged aqueous droplets optionally comprising cellular material. For example, at least 50%, 55%, 60%, 65%, 70%, 75%, 80%, 85%, 90% or 95% of the mass or matter generated by the first device and which forms the aerosol may be in the form of droplets.

The first device may be arranged and adapted to generate aerosol wherein the Sauter mean diameter ("SMD", d32) of the aerosol is in a range: (i) <5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i) <50; (ii) 50-100; (iii) 100-150; (iv) 150-200; (v) 200-250 (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating the aerosol, the aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise biological tissue, biological matter, a bacterial colony or a fungal colony, optionally wherein the biological tissue comprises human and/or non-human animal tissue.

The biological tissue may comprise in vivo biological tissue, ex vivo biological tissue, or in vitro biological tissue.

The biological tissue may comprise: (i) adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The first device may comprise a point of care ("POC"), diagnostic or surgical device.

The method may further comprise ionising at least some of the aerosol, smoke or vapour so as to generate analyte ions.

The method may further comprise directing at least some of the aerosol, smoke or vapour into a vacuum chamber of a mass spectrometer.

The method may further comprise ionising at least some the aerosol, smoke or vapour within a or the vacuum chamber of the mass spectrometer so as to generate a plurality of analyte ions.

The method may further comprise causing the aerosol, smoke or vapour to impact upon a collision surface located within a vacuum chamber of the mass spectrometer so as to generate a plurality of analyte ions.

The method may further comprise mass analysing the aerosol, smoke or vapour or analyte ions derived from the aerosol, smoke or vapour in order to obtain mass spectrometric data and/or ion mobility data.

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

The method may further comprise analysing the mass spectrometric data and/or ion mobility data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in the target; (vi) to confirm the identity or authenticity of the target; (vii) to determine whether or not one or more impurities, illegal substances or undesired substances are present in the target; (viii) to determine whether a human or animal patient is at an increased risk of suffering an adverse outcome; (ix) to make or assist in the making a diagnosis or prognosis; and (x) to inform a surgeon, nurse, medic or robot of a medical, surgical or diagnostic outcome.

The step of analysing the mass spectrometric data and/or ion mobility data may comprise performing a supervised or unsupervised multivariate statistical analysis of the mass spectrometric data.

The multivariate statistical analysis may be selected from the group consisting of: (i) principal component analysis ("PCA"); and (ii) linear discriminant analysis ("LDA").

The step of analysing the mass spectrometric data and/or ion mobility data may further comprise analysing a profile of the aerosol, smoke or vapour or a profile of ions derived from the aerosol, smoke or vapour.

The profile may be selected from the group consisting of: (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; (viii) a phosphatidylinositol (PI) profile; or (ix) a triglyceride (TG) profile.

According to another aspect there is provided an apparatus for analysis comprising:

a tool comprising a first device located within a tubing or a housing, wherein the tubing or the housing comprises a tool deployment opening and one or more separate aspiration ports.

The first device may comprise one or more electrodes.

The tool may comprise an electrosurgical tool.

The tool may comprise an optical fibre which may optionally be coupled to a laser source.

The tool may comprise a pulsed plasma RF tool such as a PlasmaBlade® tool.

The first device may generate aerosol, smoke or vapour from the target by a rapid evaporative ionisation mass spectrometry technique.

From a further aspect therefore there is provided apparatus for performing rapid evaporative ionisation mass spectrometry ("REIMS") comprising:

an electrosurgical tool comprising one or more electrodes located within a tubing or a housing, wherein the tubing or the housing comprises a tool deployment opening and one or more separate aspiration ports.

The various embodiments are particularly advantageous in that the provision of one or more aspiration ports (which are separate and distinct from the main tool deployment opening at the end of the tubing or housing) allows surgical smoke or aerosol to be aspirated into the tubing or housing and then to be passed to a mass spectrometer for analysis. This is advantageous since the main tool deployment opening at the end of the tubing or housing will tend to be blocked by e.g. a polyp which is being removed. It will be appreciated therefore that the aspiration ports are generally suitable for aspirating the aerosol, smoke or vapour generated from the target.

The surgical smoke or aerosol which is aspirated into the tubing or housing may be directed into a vacuum chamber of the mass spectrometer and may be ionised within the vacuum chamber of the mass spectrometer by colliding with a collision surface which may heated. The resulting analyte ions may then be mass analysed. As a result, a user of the tool or electrosurgical tool (e.g. a surgeon or specialist nurse) can be provided with real time information concerning the nature or type of the tissue which is being resected. The various embodiments therefore allows a surgeon to determine that all cancerous or potentially cancerous tissue has been removed and also helps to prevent an unnecessary amount of healthy tissue from being removed. The various embodiments are therefore able to play an important role in reducing the number of deaths due to gastro-intestinal cancer and to help prevent re-intervention due to incomplete excision of cancerous or potentially cancerous tissue.

The one or more electrodes may comprise a snare.

The snare may comprise a polypectomy snare.

The one or more electrodes may comprise one or more hooks, one or more grabbers, one or more blades, one or more knives, one or more serrated blades, one or more probes, one or more biopsy tools, one or more robotic tools, one or more pincers, one or more electrosurgical pencils, one or more forceps, one or more bipolar forceps, one or more coagulation devices, one or more irrigation devices or one or more imaging tools.

The one or more electrodes may comprise a monopolar device.

A separate return electrode may also be provided.

According to an alternative embodiment, the one or more electrodes may comprise a bipolar device.

The one or more electrodes may comprise: (i) a monopolar device, wherein the apparatus optionally further comprises a separate return electrode; (ii) a bipolar device; or (iii) a multi phase RF device, wherein the apparatus optionally further comprises a separate return electrode or electrodes.

According to another embodiment the first device may comprise a pulsed plasma RF tool such as a PlasmaBlade® tool.

According to an embodiment the first device may comprise either: (i) an electrode, optionally a needle electrode, which is extendable from and/or retractable within the tubing or housing; or (ii) an optical fibre for directing laser radiation on to tissue or another surface, wherein the optical fibre is extendable from and/or retractable within the tubing or housing.

The tool or electrosurgical tool may initially be deployed, in use, with the first device (e.g. the one or more electrodes or optical fibre) at least partially retracted within the tubing or the housing.

The first device (e.g. the one or more electrodes or optical fibre) may be deployed, in use, so that the first device at least partially extends beyond the tool deployment opening.

The first device (e.g. the one or more electrodes or optical fibre) may be deployed, in use, so that the first device contacts or otherwise interacts with tissue or other matter which is desired to be removed, resected or sampled.

The first device (e.g. the one or more electrodes or optical fibre) may be partially retracted, in use, so that the first device captures or securely fastens around tissue or other matter which is desired to be removed, resected or sampled.

The apparatus may further comprise an endoscope.

The endoscope may further comprise a light or an illumination device.

The tool (one or more electrodes or optical fibre) or electrosurgical tool may be deployed, in use, through a port in the endoscope.

The tool or electrosurgical tool may be activated in use.

The apparatus may further comprise a device arranged and adapted to apply an RF voltage to the first device (e.g. the one or more electrodes).

The RF voltage may have an amplitude, a peak to peak voltage or a RMS voltage selected from the group consisting of: (i) about <100 V; (ii) about 100-200 V; (iii) about 200-300 V; (iv) about 300-400 V; (v) about 400-500 V; (vi) about 500-600 V; (vii) about 600-700 V; (viii) about 700-800 V; (ix) about 800-900 V; (x) about 900-1000 V; and (xi) about >1 kV.

The RF voltage may have a frequency selected from the group consisting of: (i) < about 1 kHz; (ii) about 1-2 kHz; (iii) about 2-3 kHz; (iv) about 3-4 kHz; (v) about 4-5 kHz; (vi) about 5-6 kHz; (vii) about 6-7 kHz; (viii) about 7-8 kHz; (ix) about 8-9 kHz; (x) about 9-10 kHz; (xi) about 10-20 kHz; (xii) about 20-30 kHz; (xiii) about 30-40 kHz; (xiv) about 40-50 kHz; (xv) about 50-60 kHz; (xvi) about 60-70 kHz; (xvii) about 70-80 kHz; (xviii) about 80-90 kHz; (xix) about 90-100 kHz; (xx) about 100-200 kHz; (xxi) about 200-300 kHz; (xxii) about 300-400 kHz; (xxiii) about 400-500 kHz; (xxiv) about 500-600 kHz; (xxv) about 600-700 kHz; (xxvi) about 700-800 kHz; (xxvii) about 800-900 kHz; (xxviii) about 900-1000 kHz; (xxix) about 1-2 MHz; and (xxx) about >2 MHz.

The one or more aspiration ports may be arranged in a regular pattern or in an irregular manner along the length of the tool or electrosurgical tool.

At least some of the aspiration ports may extend at least partially outwardly from the tubing or the housing.

At least some of the aspiration ports may be at least partially recessed within the tubing or the housing.

At least some of the aspiration ports may be arranged in rows wherein aspiration ports in a first row are staggered relative to aspiration ports in a second adjacent row.

The apparatus may further comprise a device arranged and adapted to aspirate analyte, smoke, fumes, liquid, gas, surgical smoke, aerosol or vapour through the one or more aspiration ports.

The device may be arranged and adapted to aspirate the analyte, smoke, fumes, liquid, gas, surgical smoke, aerosol or vapour through the one or more aspiration ports in a substantially continuous manner.

The device may be arranged and adapted to aspirate the analyte, smoke, fumes, liquid, gas, surgical smoke, aerosol or vapour through the one or more aspiration ports in a substantially pulsed, discontinuous or irregular manner.

The device may be arranged and adapted to aspirate the analyte, smoke, fumes, liquid, gas, surgical smoke, aerosol or vapour through the one or more aspiration ports substantially only when an applied voltage or potential (e.g. an electrosurgical cutting applied voltage or potential) is supplied to the tool or electrosurgical tool or the tool is otherwise energised.

The apparatus may further comprise a control system which is arranged and adapted to vary an aspiration duty cycle during the course of a surgical, non-surgical or other procedure.

The first device may comprise an ambient ion source.

For instance, the first device may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electroflow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

According to another aspect there is provided a mass spectrometer and/or ion mobility separator comprising apparatus as described above.

The mass spectrometer and/or ion mobility separator may further comprise tubing which is arranged and adapted to pass the analyte, smoke, fumes, liquid, gas, surgical smoke, aerosol or vapour into a vacuum chamber of a mass spectrometer.

The mass spectrometer and/or ion mobility separator may further comprise a collision surface located within a vacuum chamber of the mass spectrometer.

The collision surface may be arranged and adapted so that at least some of the analyte, smoke, fumes, liquid, gas, surgical smoke, aerosol or vapour is ionised upon impact with the collision surface in order to form analyte ions.

The mass spectrometer and/or ion mobility separator may further comprise a mass analyser and/or ion mobility separator which is arranged and adapted to mass analyse and/or ion mobility analyse the analyte ions.

The mass spectrometer and/or ion mobility separator may further comprise a heating device which is arranged and adapted to heat the collision surface.

The heating device may be arranged and adapted to heat the collision surface to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The mass spectrometer and/or ion mobility separator may further comprise a device arranged and adapted to add a matrix to the analyte, smoke, fumes, liquid, gas, surgical smoke, aerosol or vapour.

The matrix may added, in use, to the analyte, smoke, fumes, liquid, gas, surgical smoke, aerosol or vapour prior to the analyte, smoke, fumes, liquid, gas, surgical smoke, aerosol or vapour impacting upon the collision surface.

The matrix may selected from the group consisting of: (i) a solvent for the analyte, smoke, fumes, liquid, gas, surgical smoke, aerosol or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

The matrix may comprise a lockmass or calibration compound.

The mass spectrometer and/or ion mobility separator may further comprise a device which is arranged and adapted to provide real time and/or delayed information to a user of the tool or electrosurgical tool.

The information may comprise mass spectral information and/or tissue classification information.

The mass spectrometer and/or ion mobility separator may further comprise a device which is arranged and adapted to generate feedback and/or an alarm and/or an alert to a user of the tool or electrosurgical tool that tissue or other matter from an undesired target region or area is being mass analysed.

The mass spectrometer may further comprise a device which is arranged and adapted to reduce or stop electrical power to the tool or electrosurgical tool in the event that tissue or other matter from an undesired target region or area is being mass analysed.

The mass spectrometer and/or ion mobility separator may further comprise a device which is arranged and adapted to generate feedback and/or an alarm and/or an alert to a user of the tool or electrosurgical tool that the tool or electrosurgical tool is operating in and/or is located in an undesired target region or area.

The mass spectrometer and/or ion mobility separator may further comprise a device which is arranged and adapted to reduce or stop electrical power to the tool or electrosurgical tool in the event that the tool or electrosurgical tool is operating in and/or is located in an undesired target region or area.

For example, according to an embodiment a determination may be made that the tool or electrosurgical tool is cutting through a specific type of tissue such as muscle. In the case of a bowel operation a warning may be generated indicating that there is a potential danger of perforating the bowel.

It will be appreciated that an apparatus or mass spectrometer and/or ion mobility separator according to any of the above aspects and embodiments may further be arranged and adapted to perform or to be utilised within any of the method steps described above, at least to the extent that they are not mutually incompatible.

According to another aspect there is provided a method of electrosurgery comprising:

providing a rapid evaporative ionisation mass spectrometry ("REIMS") electrosurgical tool comprising one or more electrodes located within a tubing or a housing, wherein the tubing or the housing comprises a tool deployment opening and one or more separate aspiration ports;

contacting biological tissue with the electrosurgical tool and activating the electrosurgical tool so as to generate analyte, smoke, fumes, liquid, gas, surgical smoke, aerosol or vapour;

aspirating the analyte, smoke, fumes, liquid, gas, surgical smoke, aerosol or vapour via the one or more aspiration ports;

causing the analyte, smoke, fumes, liquid, gas, surgical smoke, aerosol or vapour to impact upon a collision surface located within a vacuum chamber of a mass spectrometer in order to form analyte ions; and mass analysing and/or ion mobility analysing the analyte ions.

According to another aspect there is provided electrosurgical apparatus comprising:

a rapid evaporative ionisation mass spectrometry ("REIMS") electrosurgical tool comprising one or more electrodes located within a tubing or a housing, wherein the tubing or the housing comprises a tool deployment opening and one or more separate aspiration ports;

a device arranged and adapted to activate the electrosurgical tool when the electrosurgical tool is in contact, in use, with biological tissue so as to generate analyte, smoke, fumes, liquid, gas, surgical smoke, aerosol or vapour;

a device arranged and adapted to aspirate the analyte, smoke, fumes, liquid, gas, surgical smoke, aerosol or vapour via the one or more aspiration ports; and a mass spectrometer comprising: (i) a collision surface located within a vacuum chamber of the mass spectrometer and wherein, in use, analyte, smoke, fumes, liquid, gas, surgical smoke, aerosol or vapour is arranged to impact upon the collision surface so as to form analyte ions; and (ii) a mass analyser and/or ion mobility separator for mass analysing and/or ion mobility analysing the analyte ions.

Analysing the mass spectrometric data and/or ion mobility data obtained by mass analysing and/or ion mobility analysing the aerosol, smoke or vapour or analyte ions derived from the aerosol, smoke or vapour may comprise analysing one or more sample spectra so as to classify an aerosol, smoke or vapour sample.

Analysing the one or more sample spectra so as to classify the aerosol, smoke or vapour sample may comprise supervised analysis of the one or more sample spectra and/or unsupervised analysis of the one or more sample spectra.

Analysing the one or more sample spectra so as to classify the aerosol, smoke or vapour sample may comprise using one or more of: univariate analysis; multivariate analysis; principal component analysis (PCA); linear discriminant analysis (LDA); maximum margin criteria (MMC); library-based analysis; soft independent modelling of class analogy (SIMCA); factor analysis (FA); recursive partitioning (decision trees); random forests; independent component analysis (ICA); partial least squares discriminant analysis (PLS-DA); orthogonal (partial least squares) projections to latent structures (OPLS); OPLS discriminant analysis (OPLS-DA); support vector machines (SVM); (artificial) neural networks; multilayer perceptron; radial basis function (RBF) networks; Bayesian analysis; cluster analysis; a kernelized method; and subspace discriminant analysis.

Analysing the one or more sample spectra so as to classify the aerosol, smoke or vapour sample may comprise developing a classification model or library using one or more reference sample spectra.

Analysing the one or more sample spectra so as to classify the aerosol, smoke or vapour sample may comprise performing linear discriminant analysis (LDA) after performing principal component analysis (PCA).

Analysing the one or more sample spectra so as to classify the aerosol, smoke or vapour sample may comprise performing a maximum margin criteria (MMC) process after performing principal component analysis (PCA).

Analysing the one or more sample spectra so as to classify the aerosol, smoke or vapour sample may comprise defining one or more classes within a classification model or library.

Analysing the one or more sample spectra so as to classify the aerosol, smoke or vapour sample may comprise defining one or more classes within a classification model or library manually or automatically according to one or more class or cluster criteria.

The one or more class or cluster criteria for each class may be based on one or more of: a distance between one or more pairs of reference points for reference sample spectra within a model space; a variance value between groups of reference points for reference sample spectra within a model space; and a variance value within a group of reference points for reference sample spectra within a model space.

The one or more classes may each be defined by one or more class definitions.

The one or more class definitions may comprise one or more of: a set of one or more reference points for reference sample spectra, values, boundaries, lines, planes, hyperplanes, variances, volumes, Voronoi cells, and/or positions, within a model space; and one or more positions within a class hierarchy.

Analysing the one or more sample spectra so as to classify the aerosol, smoke or vapour sample may comprise using a classification model or library to classify one or more unknown sample spectra.

Analysing the one or more sample spectra so as to classify the aerosol, smoke or vapour sample may comprise classifying one or more sample spectra manually or automatically according to one or more classification criteria.

The one or more classification criteria may comprise one or more of:

a distance between one or more projected sample points for one or more sample spectra within a model space and a set of one or more reference points for one or more reference sample spectra, values, boundaries, lines, planes, hyperplanes, volumes, Voronoi cells, or positions, within the model space being below a distance threshold or being the lowest such distance;

a position for one or more projected sample points for one or more sample spectra within a model space being one side or other of one or more reference points for one or more reference sample spectra, values, boundaries, lines, planes, hyperplanes, or positions, within the model space;

a position for one or more projected sample points for one or more sample spectra within a model space being within one or more volumes or Voronoi cells within the model space; and a probability or classification score being above a probability or classification score threshold or being the highest such probability or classification score.

Various embodiments are contemplated which relate to generating smoke, aerosol or vapour from a target (details of which are provided elsewhere herein) using an ambient ionisation ion source. The aerosol, smoke or vapour may then be mixed with a matrix and aspirated into a vacuum chamber of a mass spectrometer and/or ion mobility spectrometer. The mixture may be caused to impact upon a collision surface causing the aerosol, smoke or vapour to be ionised by impact ionization which results in the generation of analyte ions. The resulting analyte ions (or fragment or product ions derived from the analyte ions) may then be mass analysed and/or ion mobility analysed and the resulting mass spectrometric data and/or ion mobility spectrometric data may be subjected to multivariate analysis or other mathematical treatment in order to determine one or more properties of the target in real time.

According to an embodiment the first device for generating aerosol, smoke or vapour from the target may comprise a tool which utilises an RF voltage, such as a continuous RF waveform.

Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

According to various embodiments the mass spectrometer and/or ion mobility spectrometer may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated.

It will be apparent that the requirement to add a matrix or a reagent directly to a sample may prevent the ability to perform in vivo analysis of tissue and also, more generally, prevents the ability to provide a rapid simple analysis of target material.

According to other embodiments the ambient ionisation ion source may comprise an ultrasonic ablation ion source or a hybrid electrosurgical—ultrasonic ablation source that generates a liquid sample which is then aspirated as an aerosol. The ultrasonic ablation ion source may comprise a focused or unfocussed ultrasound.

Optionally, the first device comprises or forms part of an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

BRIEF DESCRIPTION OF THE DRAWINGS

Various embodiments will now be described, by way of example only, and with reference to the accompanying drawings, in which:

FIG. 4A shows mass spectra of gastric mucosa, gastric submucosa and adenocarcinoma tissue which was recorded using a modified Xevo G2-S® Q-Tof mass spectrometer (Waters®), wherein cancerous and healthy mucosa tissue feature mainly phospholipids in the 600-900 m/z range whilst submucosa feature triglyceride and phosphatidylinositol species in the 800-1000 m/z range

DETAILED DESCRIPTION

Figure 1:
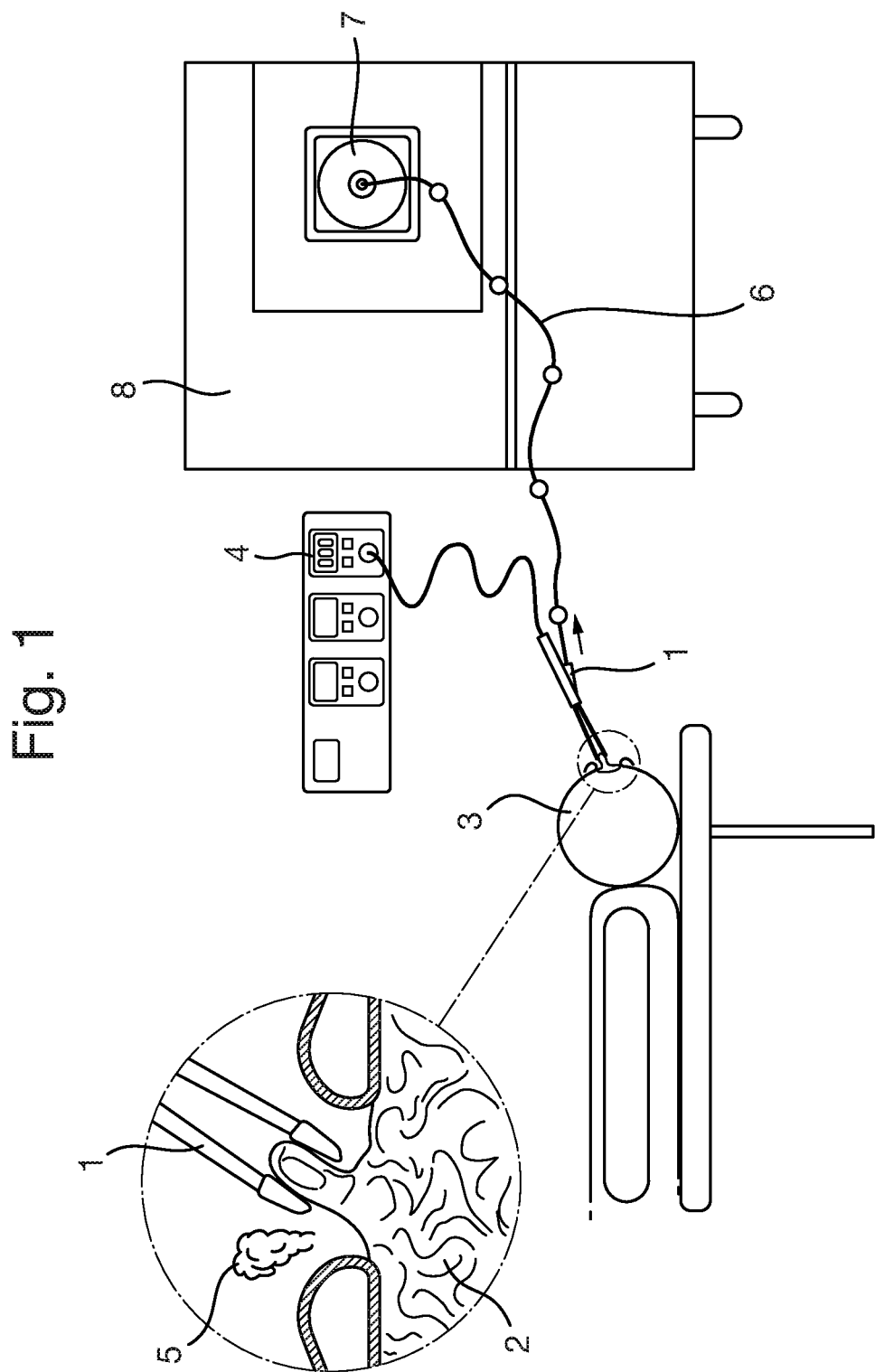
FIG. 1 illustrates a method of rapid evaporative ionisation mass spectrometry ("REIMS") wherein an RF voltage is applied to bipolar forceps resulting in the generation of an aerosol or surgical plume which is captured through an irrigation port of the bipolar forceps and is then transferred to a mass spectrometer for ionisation and mass analysis.

Various embodiments will now be described in more detail below which in general relate to an endoscope coupled with an ambient ionisation ion source.

Aerosol, surgical smoke or vapour is aspirated via one or more aspirations ports or fenestrations into a sheath which may surround a portion of the tool. The aerosol, surgical smoke or vapour may then be passed into tubing which may transfer the aerosol, surgical smoke or vapour to the inlet of a mass spectrometer. The aerosol, surgical smoke or vapour may pass into a vacuum chamber of the mass spectrometer and may be caused to impact upon a collision surface causing the aerosol, smoke or vapour to be ionised by impact ionisation and resulting in the generation of analyte ions.

The resulting analyte ions (or fragment or product ions derived from the analyte ions) may then be mass analysed and the resulting mass spectrometric data may then be subjected to multivariate analysis in order to determine one or more properties of the target (e.g. tissue) in real time.

For example, the multivariate analysis may enable a determination to be made as to whether or not a portion of tissue which is currently being resected is cancerous or not.

Ambient Ionisation Ion Sources

According to various embodiments a device is used to generate an aerosol, smoke or vapour from one or more regions of a target (e.g., in vivo tissue). The device may comprise an ambient ionisation ion source which is characterised by the ability to generate analyte aerosol, smoke or vapour from a native or unmodified target. For example, other types of ionisation ion sources such as Matrix Assisted Laser Desorption Ionisation ("MALDI") ion sources require a matrix or reagent to be added to the sample prior to ionisation.

It will be apparent that the requirement to add a matrix or a reagent to a sample prevents the ability to perform in vivo analysis of tissue and also, more generally, prevents the ability to provide a rapid simple analysis of target material.

In contrast, therefore, ambient ionisation techniques are particularly advantageous since firstly they do not require the addition of a matrix or a reagent (and hence are suitable for the analysis of in vivo tissue) and since secondly they enable a rapid simple analysis of target material to be performed.

A number of different ambient ionisation techniques are known and are intended to fall within the scope of the present invention. As a matter of historical record, Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from native (i.e. untreated or unmodified) samples. A particular advantage of the various ambient ionisation techniques which are intended to fall within the scope of the present invention is that the various ambient ionisation techniques do not require any prior sample preparation. As a result, the various ambient ionisation techniques enable both in vivo tissue and ex vivo tissue samples to be analysed without necessitating the time and expense of adding a matrix or reagent to the tissue sample or other target material.

A list of ambient ionisation techniques which are intended to fall within the scope of the present invention are given in the following table:

| Acronym | Ionisation technique |
|---|---|
| DESI | Desorption electrospray ionization |
| DeSSI | Desorption sonic spray ionization |
| DAPPI | Desorption atmospheric pressure photoionization |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |

-continued

| Acronym | Ionisation technique |
| --- | --- |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate an aerosol or plume of surgical smoke by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 µm which corresponds with the peak in the water absorption spectrum. According to various embodiments the ambient ionisation ion source may comprise a laser ablation ion source having a wavelength close to 2.94 µm on the basis of the high absorption coefficient of water at 2.94 µm. According to an embodiment the laser ablation ion source may comprise a Er:YAG laser which emits radiation at 2.94 µm.

Other embodiments are contemplated wherein a mid-infrared optical parametric oscillator ("OPO") may be used to produce a laser ablation ion source having a longer wavelength than 2.94 µm. For example, an Er:YAG pumped ZGP-OPO may be used to produce laser radiation having a wavelength of e.g. 6.1 µm, 6.45 µm or 6.73 µm. In some situations it may be advantageous to use a laser ablation ion source having a shorter or longer wavelength than 2.94 µm since only the surface layers will be ablated and less thermal damage may result. According to an embodiment a Co:MgF$_2$ laser may be used as a laser ablation ion source wherein the laser may be tuned from 1.75-2.5 µm. According to another embodiment an optical parametric oscillator ("OPO") system pumped by a Nd:YAG laser may be used to produce a laser ablation ion source having a wavelength between 2.9-3.1 µm. According to another embodiment a CO$_2$ laser having a wavelength of 10.6 µm may be used to generate the aerosol, smoke or vapour.

According to other embodiments the ambient ionisation ion source may comprise an ultrasonic ablation ion source which generates a liquid sample which is then aspirated as an aerosol. The ultrasonic ablation ion source may comprise a focused or unfocussed source.

According to an embodiment the first device for generating aerosol, smoke or vapour from one or more regions of a target may comprise an electrosurgical tool which utilises a continuous RF waveform. According to other embodiments a radiofrequency tissue dissection system may be used which is arranged to supply pulsed plasma RF energy to a tool. The tool may comprise, for example, a PlasmaBlade®. Pulsed plasma RF tools operate at lower temperatures than conventional electrosurgical tools (e.g. 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

Rapid Evaporative Ionisation Mass Spectrometry ("REIMS")

FIG. 1 illustrates a method of rapid evaporative ionisation mass spectrometry ("REIMS") wherein bipolar forceps 1 may be brought into contact with in vivo tissue 2 of a patient 3. In the example shown in FIG. 1, the bipolar forceps 1 may be brought into contact with brain tissue 2 of a patient 3 during the course of a surgical operation on the patient's brain. An RF voltage from an RF voltage generator 4 may be applied to the bipolar forceps 1 which causes localised Joule or diathermy heating of the tissue 2. As a result, an aerosol or surgical plume 5 is generated. The aerosol or surgical plume 5 may then be captured or otherwise aspirated through an irrigation port of the bipolar forceps 1. The irrigation port of the bipolar forceps 1 is therefore reutilised as an aspiration port. The aerosol or surgical plume 5 may then be passed from the irrigation (aspiration) port of the bipolar forceps 1 to tubing 6 (e.g. ⅛" or 3.2 mm diameter Teflon® tubing). The tubing 6 is arranged to transfer the aerosol or surgical plume 5 to an atmospheric pressure interface 7 of a mass spectrometer 8 and/or ion mobility spectrometer.

According to various embodiments a matrix comprising an organic solvent such as isopropanol may be added to the aerosol or surgical plume 5 at the atmospheric pressure interface 7. The mixture of aerosol 3 and organic solvent may then be arranged to impact upon a collision surface within a vacuum chamber of the mass spectrometer 8. According to one embodiment the collision surface may be heated. The aerosol is caused to ionise upon impacting the collision surface resulting in the generation of analyte ions. The ionisation efficiency of generating the analyte ions may be improved by the addition of the organic solvent. However, the addition of an organic solvent is not essential.

Analyte ions which are generated by causing the aerosol, smoke or vapour 5 to impact upon the collision surface are then passed through subsequent stages of the mass spectrometer (and/or ion mobility spectrometer) and are subjected to mass analysis in a mass analyser (and/or ion mobility analysis). The mass analyser may, for example, comprise a quadrupole mass analyser or a Time of Flight mass analyser.

Endoscope

Gastro-intestinal ("GI") cancers account for 23% of cancer-related deaths globally. Despite an increasing incidence, mortality from cancer has been decreasing over the last four decades. However, it is nonetheless estimated that a further 30-40% of these deaths can potentially be prevented. Accurate disease diagnosis and early treatment are key factors in improving cancer outcomes.

Early stage cancers and pre-malignant conditions can be successfully treated using electrocautery-based endoscopic techniques while the gold standard method for diagnosis remains white light endoscopic investigation of the GI tract with tissue biopsy.

It has been recently reported that GI cancer may be missed at endoscopy in up to 7.8% of patients who are subsequently diagnosed with cancer. A major advantage of current endoscopic procedures is that patients avoid the need for major surgery if their lesions are completely excised. However, re-intervention is necessary in up to 41% of patients due to incomplete excision.

As will become further apparent, a particular advantage of a rapid evaporative ionisation mass spectrometry endoscope and snare arrangement according to various embodiments and which will be described in more detail below is that the rapid evaporative ionisation mass spectrometry endoscope and snare arrangement enables accurate real time mass spectral data to be obtained and utilised in order to reduce mis-diagnosis rates and to improve complete resection rates.

Enhanced imaging techniques may also be used to improve diagnostic accuracy within the GI tract with particular emphasis upon spectroscopic characterization using elastic scattering spectroscopy, optical coherence tomography, multimodal imaging combining Raman spectroscopy, autofluorescence and narrow band imaging. However, none of these approaches are currently used in mainstream clinical practice.

Mass spectrometry ("MS") based identification of tissues is known using imaging techniques, sampling probe/electrospray systems and the direct ambient ionization mass spectrometry investigation of tissues.

Rapid evaporative ionization mass spectrometry ("REIMS") has emerged from this latter group as a key technology allowing in-situ real-time analysis by the utilization of electrosurgical tools as a mass spectrometry ion source.

The rapid evaporative ionisation mass spectrometry fingerprint of human tissues shows high histological specificity with 90-100% concordance with standard histology.

An embodiment relates to a real-time, robust endoscopic tissue characterisation tool which utilises rapid evaporative ionisation mass spectrometry technology.

Figure 2:
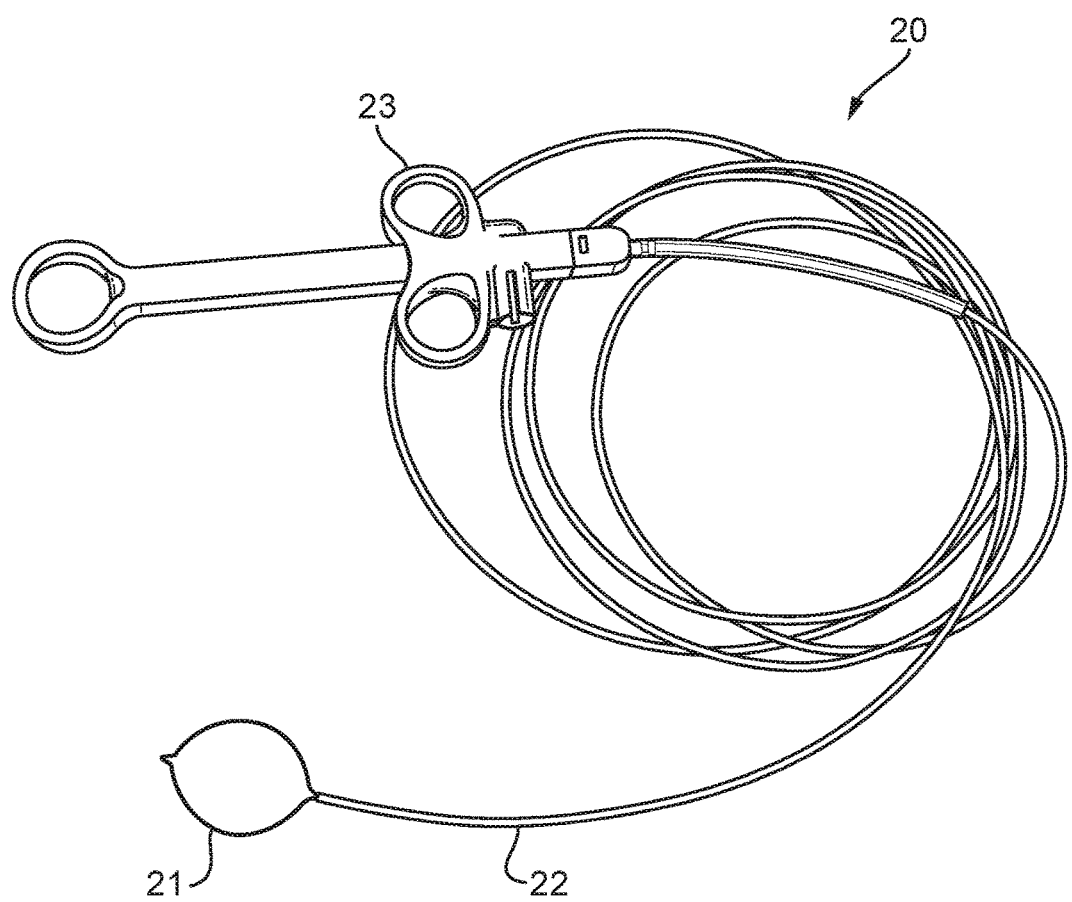
FIG. 2 shows a polypectomy snare according to an embodiment.

FIG. 2 shows a polypectomy snare 20 according to an embodiment. The snare comprises a wire loop 21 which runs through a length of tubing 22. The wire loop 21 is attached to a manipulator 23 which allows a user to close the snare around a polyp. The wire snare is connected to an RF voltage generator. The wire snare acts as an electrosurgical tool and may be used to resect polyps located e.g. in the stomach or colon. As the polypectomy snare is deployed and tightened around a polyp, the polyp effectively restricts or seals the end of the tubing which houses the wire snare.

It will be appreciated that the wire loop 21 may take any suitable form. In particular, standard commercially available snare wires may be employed within the polypectomy snares described herein. For instance, the wire loop 21 may comprise a commercially available oval braided or convex compact wire snare. It has been found that oval braided wire snares may provide a slightly more robust signal transfer and/or higher signal intensity.

When an RF voltage is applied to the wire snare, the wire snare acts as an electrosurgical tool and effectively cuts and removes the polyp. At the same time, surgical smoke or aerosol is generated which is substantially unable to pass into the end of the tubing which houses the wire snare. A particular aspect is that the tubing 22 which houses the wire snare is additionally provided with fenestrations or one or more aspiration ports 30 (as shown in FIG. 3B) which enables the surgical smoke or aerosol to be aspirated into the tubing 22 which houses the wire snare 21. The surgical smoke or aerosol is then aspirated along the length of the tubing 22 and via a connector (not shown in FIG. 2) and is passed to a vacuum chamber of a mass spectrometer 8 whereupon the surgical smoke or aerosol is ionised upon impacting a collision surface which may heated.

The resulting analyte ions are then mass analysed and real time information relating to the tissue which is being resected may be provided to a user (who may comprise a surgeon or specialist nurse). In addition to cutting the polyp away from the lining of the stomach or colon, the snare 21 may also be used to hold on to the polyp so that the polyp can be removed from the stomach, optionally analysed and then disposed of.

According to other embodiments the electrosurgical tool and optionally an associated endoscope (if provided) may be used in other body cavities and organs including the lung, nose and urethra. In particular, the endoscope may comprise a bronchoscope, a cystoscope, a rhinoscope or a nasoscope.

According to an embodiment the snare 21 may comprise a monopolar device and a relatively large pad acting as a return electrode may be placed underneath the patient so that electrical current flows from the snare electrode 21, through the patient, to the return electrode. Other embodiments are also contemplated wherein the snare electrode 21 may comprise a bipolar device such that electrical current does not flow through the patient's body. A bipolar device may be used, for example, in very sensitive operations such as brain surgery wherein it is clearly undesirable for an electrical current to flow through surrounding tissue.

According to an embodiment the snare 21 may comprise a monopolar device probe or needle probe and a relatively large pad acting as a return electrode may be placed underneath the patient so that electrical current flows from the probe electrode, through the patient, to the return electrode. Alternatively, the probe may comprise a bipolar device.

Although a monopolar or a bipolar electrode arrangement is particularly advantageous, other embodiments are also contemplated wherein the electrosurgical tool may comprise a multi-phase or 3-phase device and may comprise, for example, three or more separate electrodes or probes.

According to another embodiment a pulsed plasma RF tool such as a PlasmaBlade® tool may be used to generate the surgical smoke, aerosol or vapour.

According to another embodiment an optical fibre coupled to a laser source may be used to generate the surgical smoke, aerosol or vapour.

According to an embodiment surgical smoke or aerosol which is aspirated via the electrosurgical tool may be passed via a liquid separator or liquid trap in order to remove or reduce the amount of liquid which is onwardly transmitted to the mass spectrometer and/or ion mobility spectrometer.

A matrix may added or mixed with the analyte, smoke, fumes, liquid, gas, surgical smoke, aerosol or vapour may prior to the analyte, smoke, fumes, liquid, gas, surgical smoke, aerosol or vapour impacting upon the collision surface.

The matrix may comprise a solvent for the analyte, smoke, fumes, liquid, gas, surgical smoke, aerosol or vapour and may comprise an organic solvent and/or a volatile compound.

According to an embodiment the matrix may comprise polar molecules, water, one or more alcohols, methanol, ethanol, isopropanol, acetone or acetonitrile. Isopropanol is particularly advantageous to use.

The matrix which is added may additionally or alternatively comprise a lockmass or calibration compound.

The addition of a matrix is particularly advantageous in that dissolving analyte in the matrix eliminates intermolecular bonding between the analyte molecules. As such, when the dissolved analyte is collided with the collision surface, the dissolved analyte will fragment into droplets and any given droplet is likely to contain fewer analyte molecules than it would if the matrix were not present. This in turn leads to a more efficient generation of ions when the matrix in each droplet is evaporated.

Figure 3A:
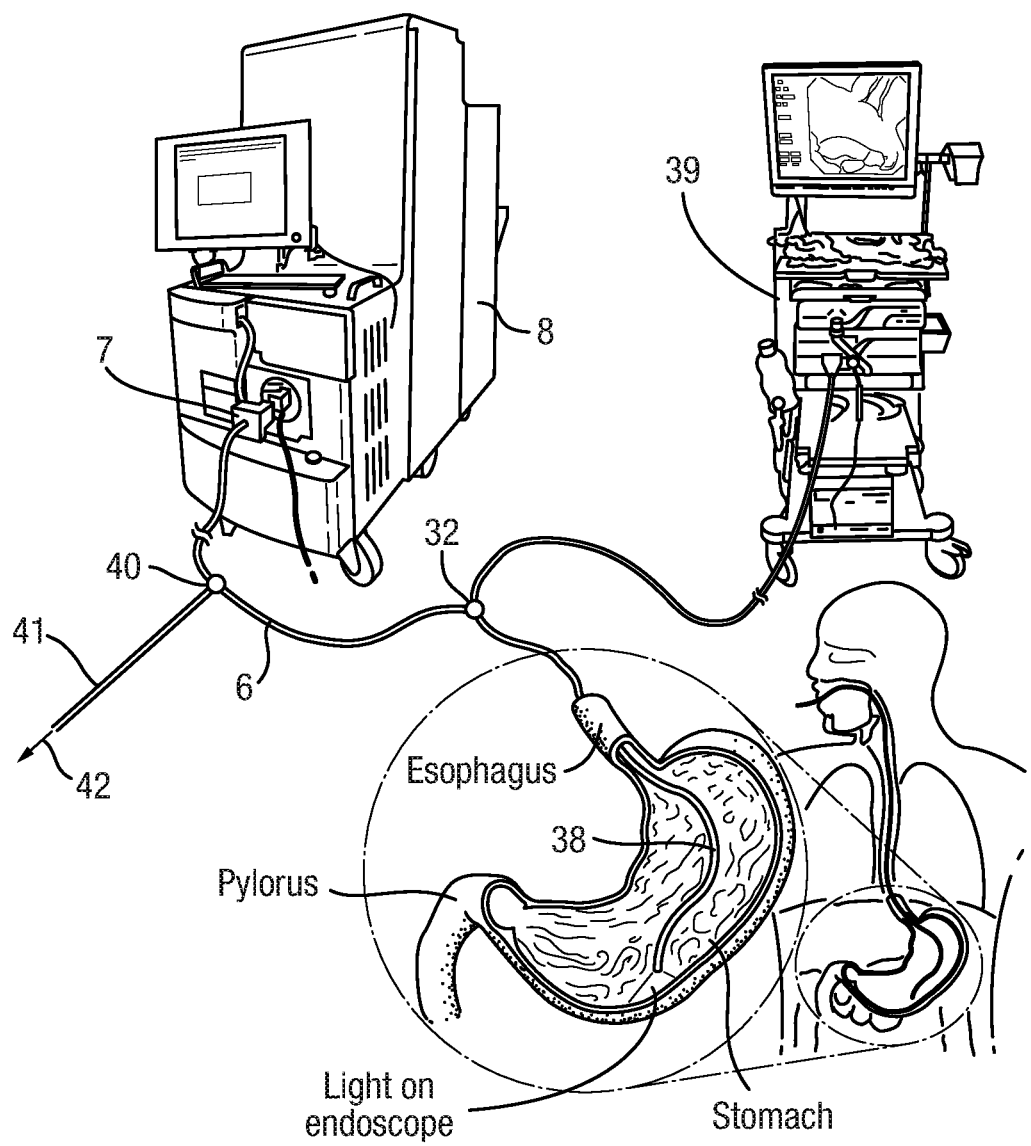
FIG. 3A shows an endoscopic experimental setup wherein endoscopic tubing is equipped with an additional T-piece in order to establish a direct connection between an electrosurgical electrode tip and a mass spectrometer for the transfer of electrosurgical aerosol and FIG. 3B shows a resection of a GI polyp according to an embodiment wherein an electrosurgical snare is used to capture a polyp using the snare loop so that the polyp is securely fastened around its base and then electrosurgical dissection is performed and the resulting surgical smoke or aerosol is aspirated through fenestrations provided in the plastic sheath of the electrosurgical tool.
Figure 3B:
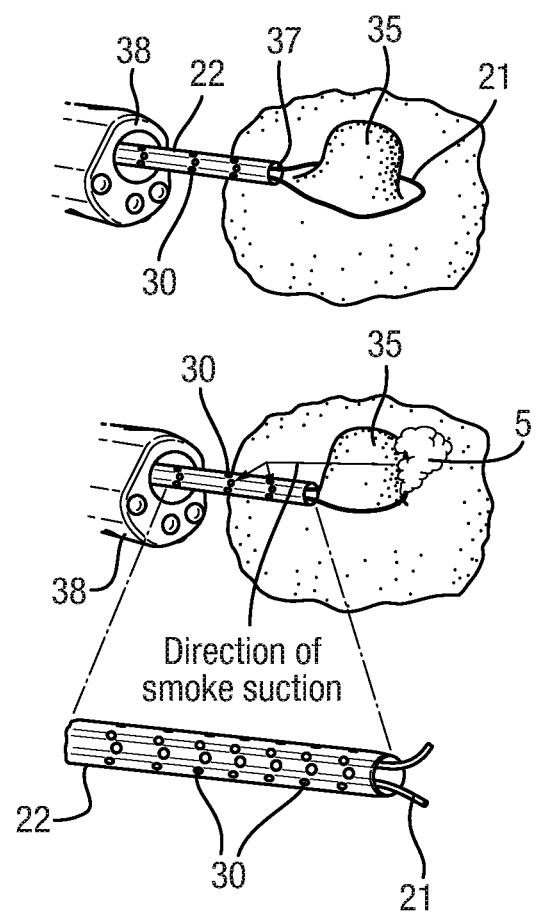

FIG. 3A shows in more detail an embodiment and shows an endoscopic polypectomy snare which is equipped with an additional T-piece connector 32 in order to establish a direct transfer line 6 between the tissue evaporation point and the atmospheric inlet 7 of a mass spectrometer 8 and/or ion mobility spectrometer (in addition to the transfer line from the endoscope 38 to an endoscopic stack 39).

The T-piece connector 32 may include a valve which only allows surgical smoke, aerosol or vapour to be transferred to the inlet 7 of the mass spectrometer 8 and/or ion mobility spectrometer when the snare (or other tool) is energised. If the snare (or other tool) is not being energised then the tube 6 in fluid communication with the snare (or other tool) may be diverted to atmosphere. The valve can thereby help to stop deflation of the bowel or gastrointestinal ("GI") tract.

According to an embodiment the endoscopic tool may be equipped with a fluid detection device 40 which may be arranged to detect fluid (e.g. mucus, bile or other bodily fluid) or saline solution travelling up the sampling tube 6. The fluid detection device 40 may be positioned at the T-piece connector 32 or at a different position along the sampling tube e.g. upstream of the T-piece connector 32 as shown in FIG. 3A.

The fluid detection device 40 may effectively form a diverter which is arranged to divert fluid or liquid to waste or suction 42 via a tube 41 in the event that fluid is detected. As a result, fluid is prevented from reaching the inlet 7 of the mass spectrometer 8 and/or ion mobility spectrometer.

The rapid evaporative ionisation mass spectrometry based endoscopic setup according to various embodiments addresses various potential problems if a conventional endoscope were attempted to be used.

In particular, the various embodiments are designed to address the problem of there being a short signal capture window (typically 1-2 seconds) coupled with the problem of seeking to aspirate aerosol from a closed cavity.

A yet further problem which the various embodiments seek to address is the problem of potential exogenous contamination from the GI tract and the need for a long sampling line 6 (>4 m) through the working channel of the endoscope 38.

The rapid evaporative ionisation mass spectrometry endoscopic setup was initially optimized and its reproducibility was assessed using a porcine stomach model. Artificial polyps were created within porcine stomach mucosa and resections were undertaken using a polypectomy snare 21 as shown in FIG. 3B. This set-up allowed for an exact simulation of a standard endoscopic resection. Since the polyp 35 completely blocks the opening or tool deployment opening 37 of the plastic sheath 22 of the snare during resection (as can be seen from FIG. 3B), the aerosol 5 produced by the resection is aspirated through fenestrations 30 which are provided on the plastic sheath 22 of the snare 21.

The provision of fenestrations 30 on the plastic sheath 22 of the rapid evaporative ionisation mass spectrometry snare 21 and which are distal from the tool deployment opening 37 of the snare are particularly advantageous since the fenestrations or aspiration ports 30 allow surgical smoke and/or aerosol to be aspirated when the tool deployment opening 37 is at least partially or totally blocked.

The aerosol particles which enter the rapid evaporative ionisation mass spectrometry sheath 22 via the fenestrations or aspiration ports 30 may then be transferred to a mass spectrometer 8 via PFTE tubing 6 which may connected to a port of the snare. The snare 21 may be connected to or extend from the proximal end of an endoscope 38. The tubing 6 may be connected directly to an inlet capillary or ion sampling orifice 7 of the mass spectrometer 8. It will be understood that the mass spectrometer 8 is distal to the point of evaporation.

Aspiration of the aerosols may be facilitated using a Venturi pump driven by standard medical air or nitrogen.

The mass spectrometer may include a modified atmospheric interface which may include a collision surface which may positioned along and adjacent to the central axis of the large opening of a StepWave® ion guide. As will be understood by those skilled in the art, a StepWave® ion guide comprises two conjoined ion tunnel ion guides. Each ion guide comprises a plurality of ring or other electrodes wherein ions pass through the central aperture provided by the ring or other electrodes. Transient DC voltages or potentials are applied to the electrodes. The StepWave® ion guide is based on stacked ring ion guide technology and is designed to maximise ion transmission from the source to the mass analyser. The device allows for the active removal of neutral contaminants thereby providing an enhancement to overall signal to noise. The design enables the efficient capture of the diffuse ion cloud entering a first lower stage which is then may focused into an upper ion guide for transfer to the mass analyser.

The collision surface located within a vacuum chamber of the mass spectrometer 8 may facilitate efficient fragmentation of molecular clusters formed in the free jet region of the atmospheric interface due to the adiabatic expansion of gas entering the vacuum chamber and the resulting drop of temperature. Other means for facilitating efficient fragmentation of molecular clusters may additionally or alternatively be provided within the vacuum chamber, for example, a collision gas may be provided in this region wherein collisions with the collision gas helps to break up the molecular clusters.

The surface-induced dissociation of supramolecular clusters may improve the signal intensity and may also alleviate the problems associated with the contamination of ion optics.

Rapid evaporative ionisation mass spectrometry spectra recorded from the porcine stomach model in the m/z range 600-1000 feature predominantly phospholipids which have been observed for all mammalian tissue types in previous rapid evaporative ionisation mass spectrometry experiments.

Various experiments were performed in order to optimise the snare tip geometry and also to optimise the number and relative positions of the fenestrations 30 on the plastic sheath 22 of the snare. An assessment of the repeatability of the analysis was also performed.

Following optimization of the sampling geometry, the rapid evaporative ionisation mass spectrometry endoscopic setup was tested on ex vivo human samples including gastric adenocarcinoma, healthy gastric mucosa and healthy gastric submucosa.

The samples were acquired from three individual patients, all of whom provided written informed consent.

Previous studies demonstrated marked differences in the rapid evaporative ionisation mass spectrometry fingerprint of healthy mucosa and cancers of the GI tract. However, for the first time healthy submucosa and GI polyps were investigated.

Significant spectral differences were observed between healthy gastric mucosa, healthy gastric submucosa and gastric cancer tissue. Spectra of healthy gastric mucosa (n=32) and gastric adenocarcinoma (n=29) featured phospholipids in the range m/z 600-900 while the gastric submucosa (n=10) featured intensive triglyceride ("TG") and phosphatidyl-inositol ("PI") species in the m/z 900-1000 range as shown in FIG. 4A.

The submucosa in the GI tract represents a connective tissue layer containing arterioles, venules and lymphatic vessels. It is made up of mostly collagenous and elastic fibers with varying amounts of adipose elements. It is hypothesised that the PI and triglycerides species observed in the m/z 900-1000 mass range are associated with these histological features present within the submucosa.

An interesting feature was observed regarding the abundance of phosphatidyl-ethanolamines and corresponding plasmalogen species. While the PEs show higher abundance, the plasmalogens are depleted in the tumour tissue, probably due to the impaired peroxisomal function of the cancer cells.

Figure 4B:
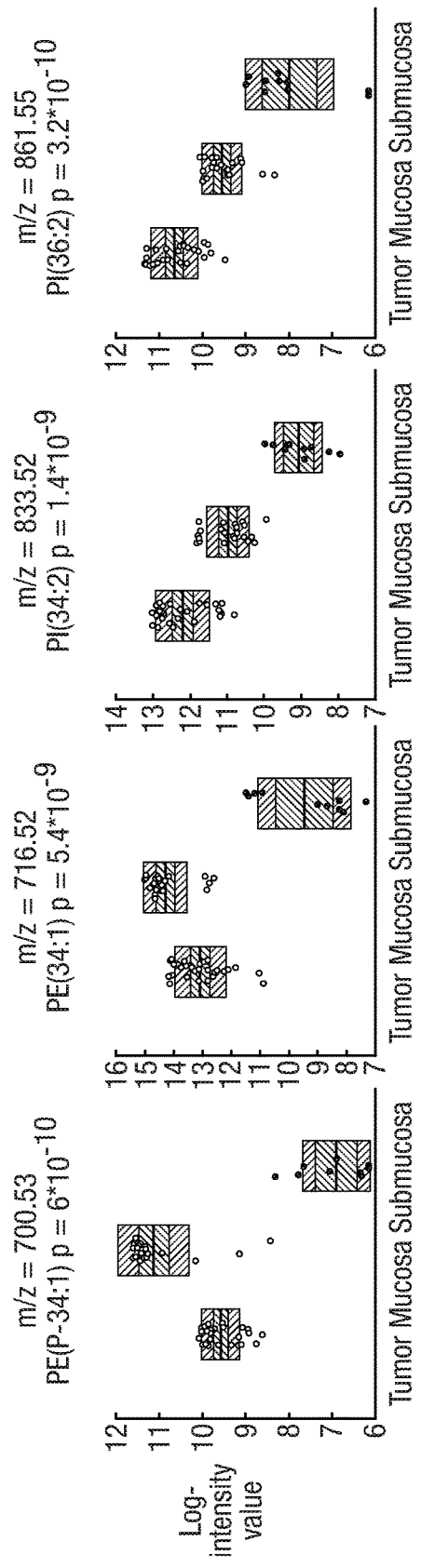
FIG. 4B shows a comparison of the abundance of selected peaks showing significant differences between cancerous and healthy tissue in the 600-900 m/z range using Kruskal-Wallis ANOVA wherein all peaks above m/z 800 are significantly different when comparing submucosa to the other two tissue types.

FIG. 4B shows a number of selected peaks which are significantly different between the healthy tissue layers and cancer tissue in the mass range 600-900. All peaks between m/z 900 to 1000 show significant differences when comparing the gastric submucosa to either adenocarcinoma or gastric mucosa.

The clear differences observed between the rapid evaporative ionisation mass spectrometry fingerprints of the submucosa and mucosal layer may according to an embodiment be exploited as a potential safety function for interventional endoscopy.

Colonoscopic procedures involving electrocautery are associated with a 9× increase in perforation risk compared to a purely diagnostic procedure. It has also been reported that endomucosal resection ("EMR") of ulcerated lesions are at higher risk of perforation. According to an embodiment the rapid evaporative ionisation mass spectrometry endoscopic method may include an alert feature such that any diathermy device is immediately stopped if there is a breach of the submucosal layer during polypectomy or endomucosal resection.

Real time and/or delayed information may be provided to a user of the electrosurgical tool that may comprise mass spectral information and/or tissue classification information. A feedback device and/or an alarm and/or an alert may also may be provided to provide a user of the electrosurgical tool with feedback and/or an alarm and/or an alert that analyte from an undesired target region or area is being analysed by the analyser or that the electrosurgical tool is operating in and/or is located in an undesired target region or area.

Electrical power to the electrosurgical tool may be reduced and/or stopped in the event that analyte from an undesired target region or area is being analysed by the analyser and/or the electrosurgical tool is operating in and/or is located in an undesired target region or area.

Development of the rapid evaporative ionisation mass spectrometry technology for this purpose advantageously helps in decreasing perforation rates and the significant morbidity associated with this complication.

Analysis of ex vivo human colonic adenocarcinoma (n=43) and healthy colonic mucosa (n=45) acquired from seven patients was conducted using a LTQ Velos® mass spectrometer at the University of Debrecen, Hungary.

Figure 5A:
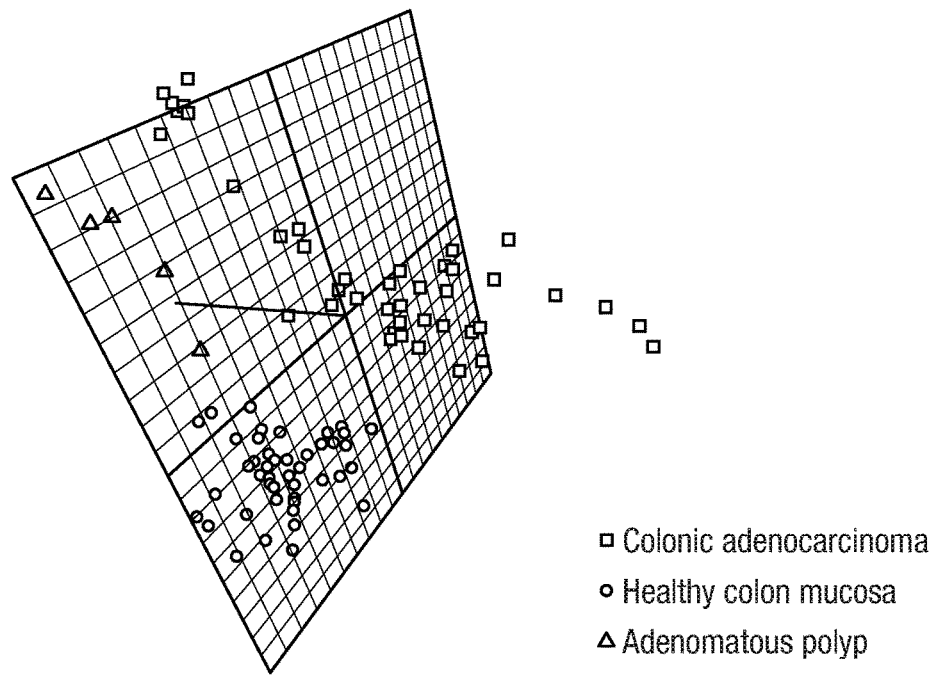
FIG. 5A shows a 3-dimensional PCA plot of human colon adenocarcinoma (n=43) and healthy colon mucosal data (n=45) acquired from seven patients using an LTQ Velos® mass spectrometer wherein the adenomatous polyps (n=5) collected from two patients were sampled ex vivo after their removal and wherein a significant difference can be observed in the PCA space between all three groups and FIG. 5B shows a 3-dimensional PCA plot of healthy gastric mucosa (n=32), gastric submucosa (n=10) and adenocarcinoma of the stomach (n=29) acquired from three patients ex vivo using a Xevo G2-S® Q-Tof mass spectrometer (Waters®) wherein significant differences between submucosa and the other two layers may be used to provide a perforation risk alert system for interventional endoscopy according to an embodiment.
Figure 5B:
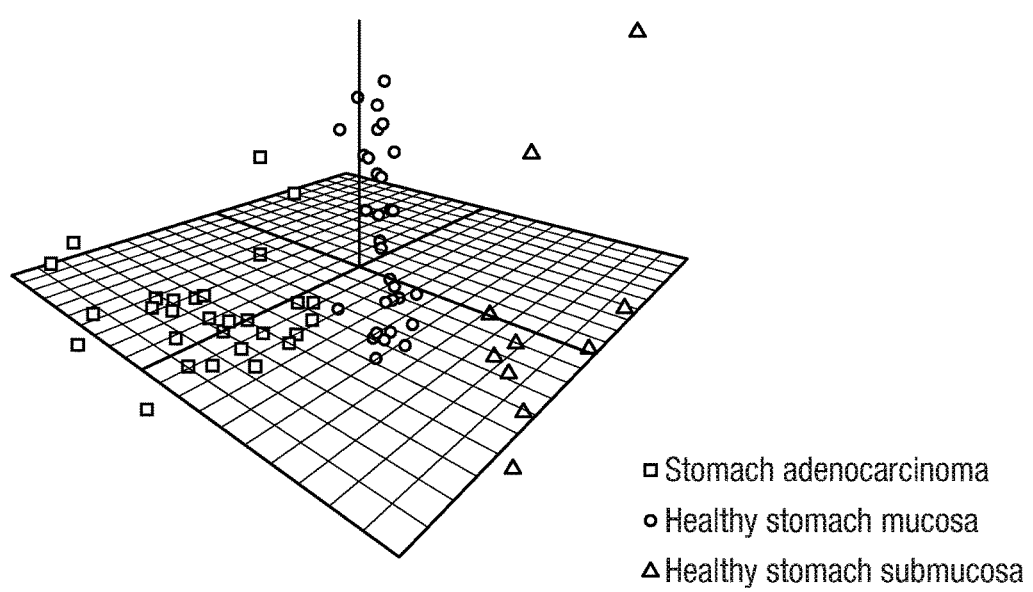

Adenomatous polyps (n=5) from two patients were also sampled ex vivo and the resulting rapid evaporative ionisation mass spectrometry data was analysed using multivariate statistical tools as shown in FIGS. 5A and 5B. In agreement with previously published rapid evaporative ionisation mass spectrometry studies, the spectra acquired from healthy mucosa and adenocarcinoma of both the stomach and colon were discovered to separate well in 3-dimensional PCA space as can be seen from FIGS. 5A and 5B. The sampled adenomatous polyps also demonstrate good separation from both healthy mucosa and malignant tissue from the colon as shown in FIG. 5A.

Figure 6B:
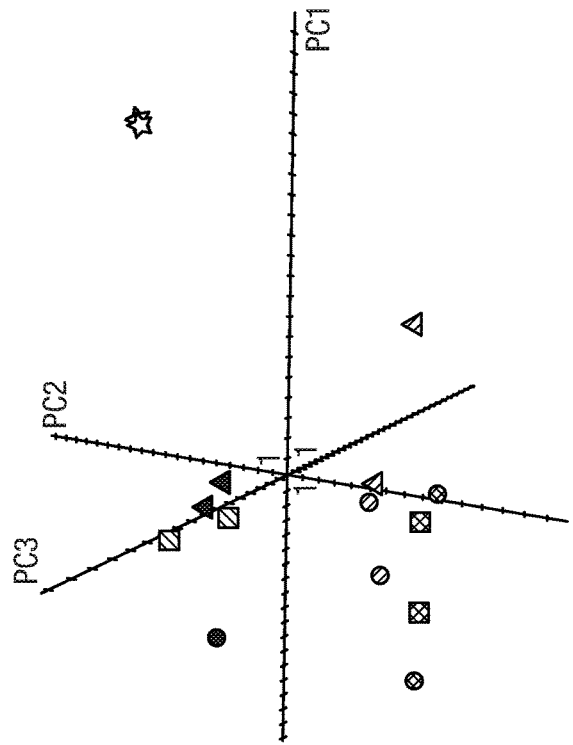
FIG. 6A shows in vivo utilization of a rapid evaporative ionisation mass spectrometry compatible endoscope system according to an embodiment and sampling points taken from three patients undergoing colonoscopy and FIG. 6B shows the sampling points depicted on a 3-dimensional PCA plot wherein the spectra acquired in vivo when the polyps were removed localize in a different part of space whilst all other mucosal spectra are quasi uniformly independent from the sampling location.
Figure 6A:
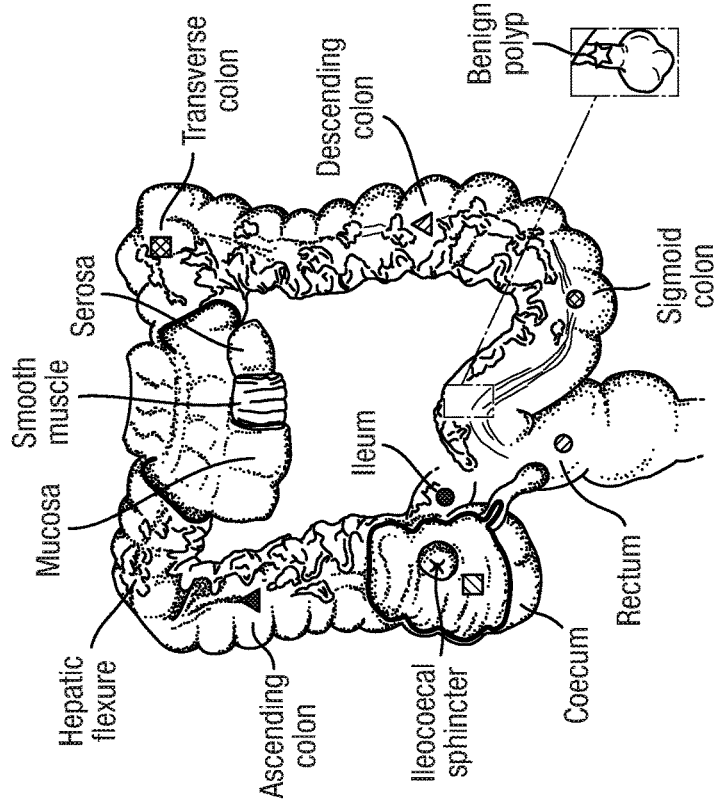

Following the proof of concept analysis of ex vivo samples, the rapid evaporative ionisation mass spectrometry endoscopic method was also tested in vivo on three consecutive patients referred for colonoscopy. FIG. 6A shows in vivo utilization of a rapid evaporative ionisation mass spectrometry compatible endoscope system according to an embodiment and sampling points taken from three patients undergoing colonoscopy and FIG. 6B shows the sampling points depicted on a 3-dimensional PCA plot wherein the spectra acquired in vivo when the polyps were removed localize in a different part of space whilst all other mucosal spectra are quasi uniformly independent from the sampling location.

Different regions of the colon and rectum were sampled during the colonoscopy procedures. The first and third patients had evidence of colonic polyps and these were confirmed to be benign. The second patient had evidence of a normal colon with no visible polyps. The mucosal layer showed uniform spectral pattern independently from anatomical location. However, colonic polyps showed marked differences from the healthy mucosal layer as shown in FIG. 6B. This is in agreement with the findings of previous ex vivo studies.

The data presented herewith demonstrates the significant advantages in using the rapid evaporative ionisation mass spectrometry technique as a real-time diagnostic tool in endoscopy in accordance with an embodiment.

The rapid evaporative ionisation mass spectrometry compatible endoscope and snare has been tested in both ex vivo and in vivo settings without the need for major modification of standard approved clinical equipment. The method has been optimised to account for the short signal capture window that occurs with endoscopic resectional procedures and also to address technical challenges associated with long ion transfer distances and potential aspiration of gastric/intestinal content.

The rapid evaporative ionisation mass spectrometry compatible endoscope 38 and snare 21 has successfully been shown to be capable of differentiating between healthy mucosa, adenomae and GI cancer based on their individual lipodomic spectral profiles. Furthermore, the significant differences demonstrated between healthy mucosal and submucosal layers of the GI tract indicate that rapid evaporative ionisation mass spectrometry can also be utilized to avoid the damaging of smooth muscle layer and consequent perforation in course of interventional endoscopy.

Rapid evaporative ionisation mass spectrometry technology has also been demonstrated to be able to identify microorganisms. Accordingly the rapid evaporative ionisation mass spectrometry endoscope may be used to analyser in situ bacteria. This is of particular interest since the composition and metabolic activity of gut microbiota has been associated with the pathogenesis of cancer, diabetes, obesity, hypertension and autism.

The rapid evaporative ionisation mass spectrometry endoscope 38 and snare 21 may be used as a general screening tool in order to help the assessment of the risk of developing a wide variety of diseases and also to enable preventive measures to be taken in a timely manner. The rapid evaporative ionisation mass spectrometry endoscope 38 and snare 21 may also be used, for example, for testing of faecal or mucal material.

The techniques described above are presented in the context of an embodiment utilising rapid evaporative ionisation mass spectrometry. However, it will be appreciated that the techniques and apparatus described herein are not limited to rapid evaporative ionisation mass spectrometry devices and may also be extended to other ambient ion sources. For example, a tool having fenestrations or aspiration ports may be provided as part of a laser surgery probe for aspirating aerosol, smoke or vapour generated using the laser. Further details of known ambient ion sources that may be suitable for use with the techniques and apparatus described herein are presented below.

The endoscopic tool may be used to help distinguish between healthy, potentially cancerous, cancerous, potentially diseased or diseased biological tissue or the margins or bounds of a tumour.

The cancerous biological tissue or the tumour may comprise: (i) grade I, grade II, grade III or grade IV cancerous tissue; (ii) metastatic cancerous tissue; (iii) mixed grade cancerous tissue; or (iv) a sub-grade cancerous tissue.

The endoscopic tool may also be used to identify whether or not a patient is suffering from irritable bowel syndrome ("IBS"), inflammatory bowel disease ("IBD"), Chron's disease or ulcerative colitis ("UC").

Experimental

For the experiments described above, a commercially available polypectomy snare (Olympus® Model No. SD-210U-15) having a working length of about 2300 mm, minimum channel size about 2.8 mm, opening diameter about 15 mm and wire thickness about 0.47 mm was equipped with an additional T-piece 32 in order to establish connection with a ⅛" OD 2 mm ID PFTE tubing 6 between the tissue evaporation point and the atmospheric inlet 7 of a mass spectrometer 8 (Xevo G2-S® Q-TOF, Waters®, Manchester, UK, and a LTQ Velos® linear ion trap mass spectrometer, Thermo Fischer Scientific®, Bremen, Germany).

The snare 21 was used with a commercially available endoscope 38 (Olympus®, Tokyo, Japan) and the associated endoscopic stack 39 was coupled with an electrosurgical generator (Valleylab Surgistat II®).

The endoscopic plume 5 generated during the removal of polyps was captured through the fenestrations 30 on the rapid evaporative ionisation mass spectrometry snare 21. The endoscopic plume 5 was then transferred to the mass spectrometer 8 through the endoscope housing and via PFTE tubing 6 which was coupled directly to the inlet capillary 7 of a mass spectrometer 8 using the internal vacuum of the mass spectrometer for plume capturing.

High resolution mass spectrometry was performed in negative ion mode between m/z 150-1500 range.

Written, informed consent was obtained from all patients who provided tissue samples. Ethical approval was obtained from the Hungarian National Scientific Research Ethical Committee (Ref number 182/PI/10) and the National Research Ethics Service, UK (Ref number: 11/LO/0686).

The data analysis workflow for the separation of healthy, cancerous and adenomatous polyps of the gastrointestinal tract included the construction of a tissue specific spectral database followed by multivariate classification and spectral identification algorithms in a known manner.

Figure 7:
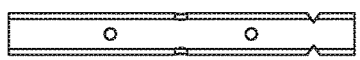
FIG. 7 shows three different configurations of fenestrations on a snare tubing that were tested according to an embodiment.
Figure 7:
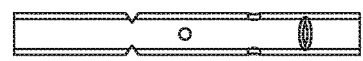
Figure 7:
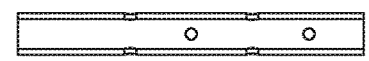

The test studies described above using an Olympus disposable snare 21 on ex vivo oesophageal gastric and colorectal samples provided good quality signals with reasonable intensities; particularly for relatively large samples. The effect of the snare 21 and/or fenestration geometry was investigated to attempt to optimize the signal transfer. Three different configurations of fenestrations 30 (shown in FIG. 7) were tested in combination with two different types of commercially available snare wire 21 (oval braided and convex compact) to give a total of six different snare configurations.

Figure 8:
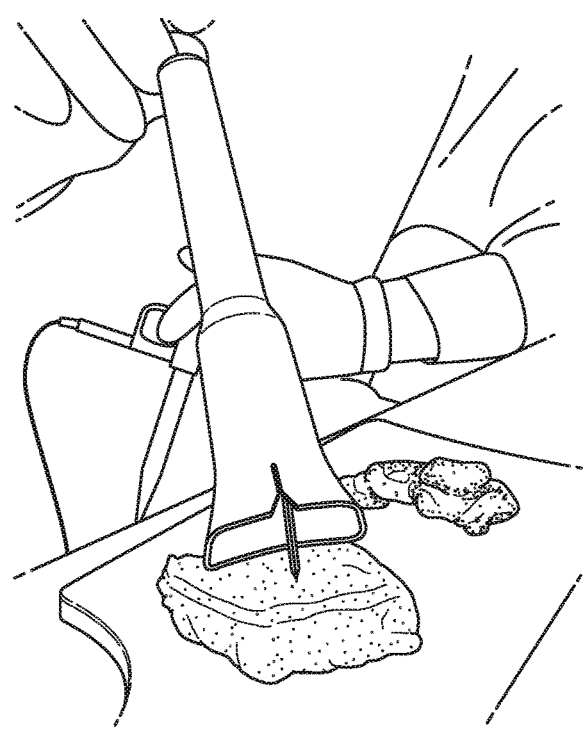
FIG. 8 illustrates an ex vivo testing method which was arranged to simulate an endoscopic environment.

Systematic experiments were carried out for each of the six snare configurations on porcine muscle tissue and normal human colorectal mucosa tissue. To mimic the conditions of the endoscope environment a long funnel-tube was held over the tissue with the snare threaded through it as shown in FIG. 8. An isopropanol matrix was added to the aerosol/smoke at the mass spectrometer inlet 7. In order to optimize the signal, the experimental set-up was altered by not using a Venturi gas flow. This increased signal intensity but resulted in approximately a six second delay from snare use to spectral signal received due to the relatively slow transit of the aerosol/smoke through the tubing 6. High-resolution mass spectrometry was performed in negative-ion mode in the m/z 150-1500 range.

Figure 9:
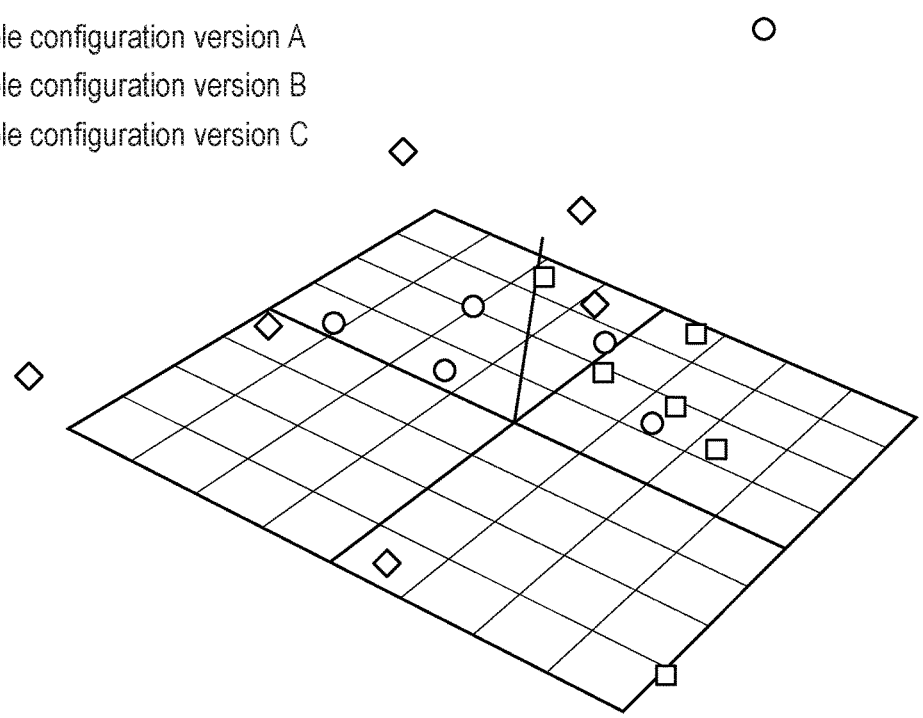
FIG. 9 shows a linear discriminant analysis plot comparing the testing for the three different configurations of fenestration illustrated in FIG. 7.
Figure 10:
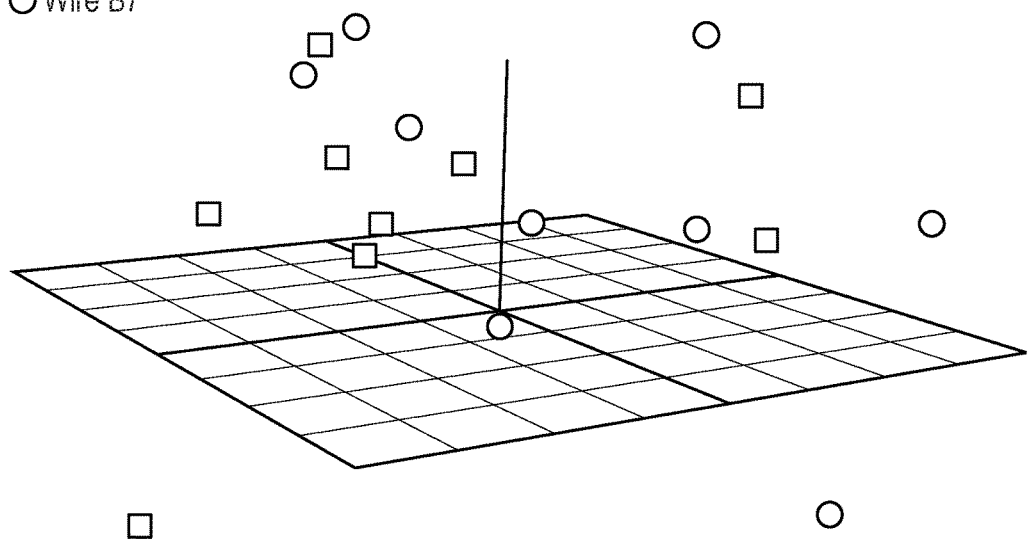
FIG. 10 shows a linear discriminant analysis plot comparing the testing of two different wire snare types.

With the isopropanol matrix and no Venturi gas flow, phospholipid peaks of sufficiently high intensity (of the order of $10^3$) were seen for each of the snare configurations tested. There was no apparent difference in the spectra obtained with any of the different hole configurations shown in FIG. 7, with robust signals being obtained for all three hole configurations, and this was confirmed by linear discriminant analysis (see the plot in FIG. 9). The different wire snare types also produced very similar results but a slightly higher signal intensity was obtained for the phospholipid peaks of interest in the 600-1000 m/z region using the oval braided wire snare compared to the convex compact wire snare (see the linear discriminant analysis plot in FIG. 10).

Analysing Sample Spectra

A list of analysis techniques which are intended to fall within the scope of the present invention are given in the following table:

Analysis Techniques
Univariate Analysis
Multivariate Analysis
Principal Component Analysis (PCA)
Linear Discriminant Analysis (LDA)
Maximum Margin Criteria (MMC)
Library Based Analysis
Soft Independent Modelling Of Class Analogy (SIMCA)
Factor Analysis (FA)
Recursive Partitioning (Decision Trees)
Random Forests
Independent Component Analysis (ICA)
Partial Least Squares Discriminant Analysis (PLS-DA)
Orthogonal (Partial Least Squares) Projections To Latent Structures (OPLS)
OPLS Discriminant Analysis (OPLS-DA)
Support Vector Machines (SVM)

(Artificial) Neural Networks
Multilayer Perceptron
Radial Basis Function (RBF) Networks
Bayesian Analysis
Cluster Analysis
Kernelized Methods
Subspace Discriminant Analysis
K-Nearest Neighbours (KNN)
Quadratic Discriminant Analysis (QDA)
Probabilistic Principal Component Analysis (PPCA)
Non negative matrix factorisation
K-means factorisation
Fuzzy c-means factorisation
Discriminant Analysis (DA)

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

Figure 11:
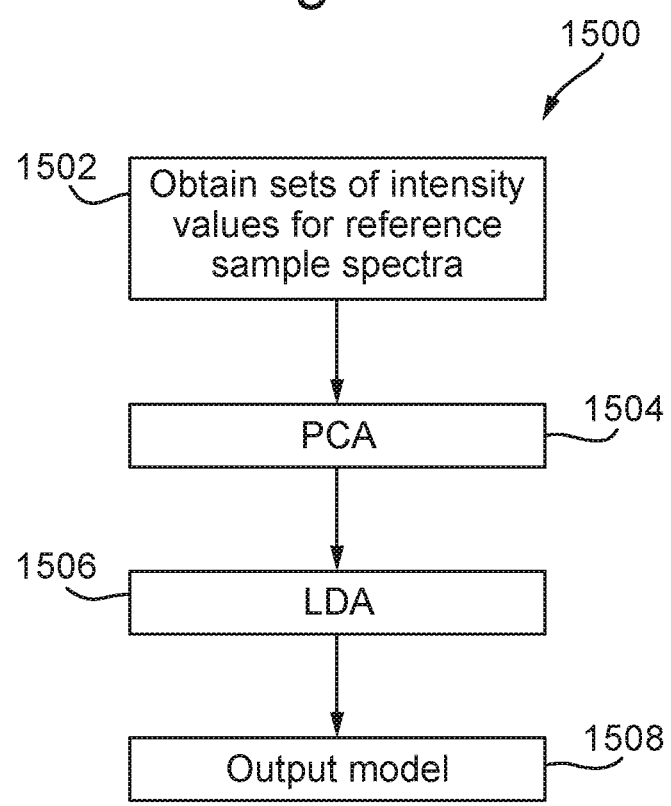
FIG. 11 shows a method of analysis that comprises building a classification model according to various embodiments.

FIG. 11 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

Figure 12:
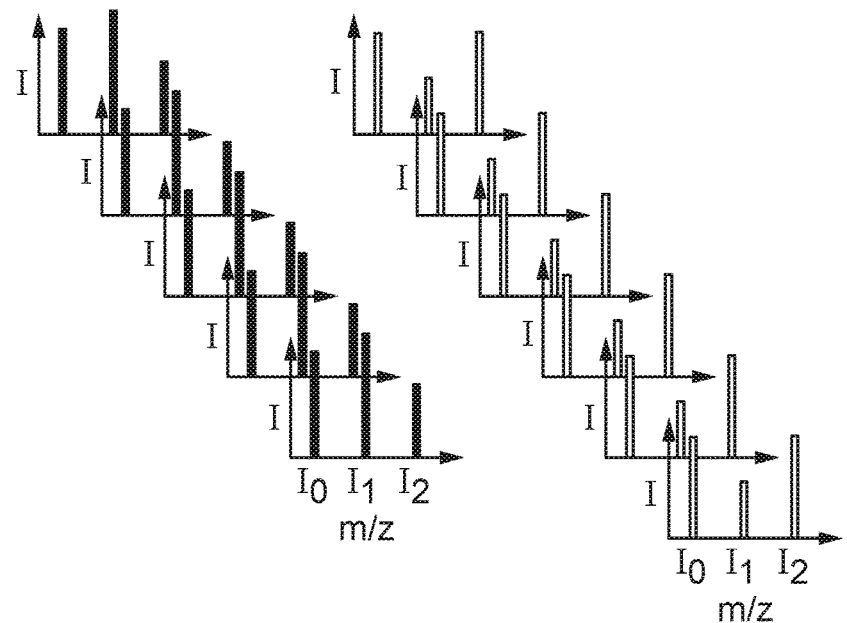
FIG. 12 shows a set of reference sample spectra obtained from two classes of known reference samples.

FIG. 12 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 13:
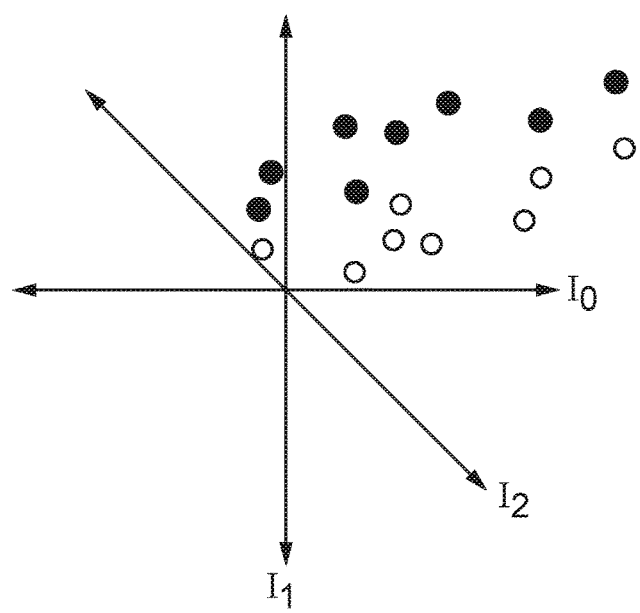
FIG. 13 shows a multivariate space having three dimensions defined by intensity axes, wherein the multivariate space comprises plural reference points, each reference point corresponding to a set of three peak intensity values derived from a reference sample spectrum.

FIG. 13 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 14:
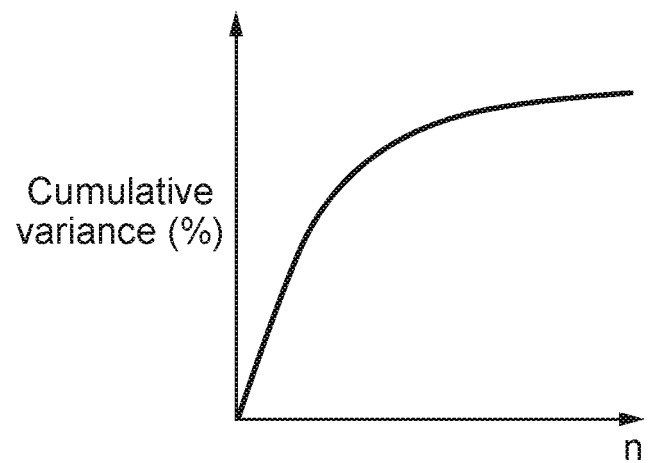
FIG. 14 shows a general relationship between cumulative variance and number of components of a PCA model.

FIG. 14 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \qquad (1)$$

Figure 15:
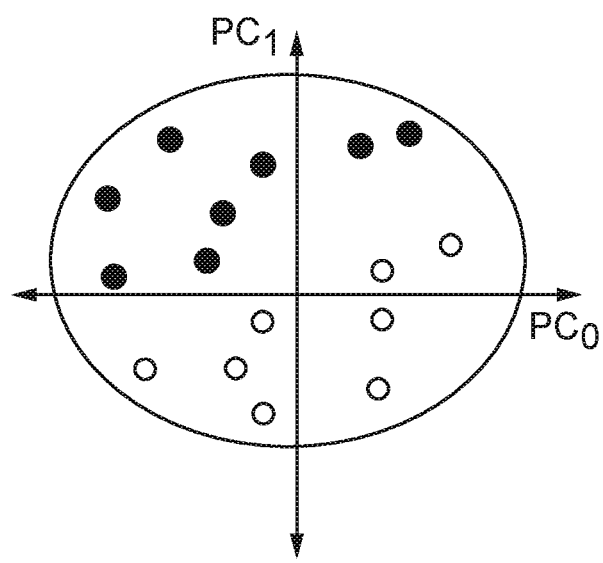
FIG. 15 shows a PCA space having two dimensions defined by principal component axes, wherein the PCA space comprises plural transformed reference points or scores, each transformed reference point or score corresponding to a reference point of FIG. 13.

FIG. 15 shows the resultant PCA space for the reference sample spectra of FIGS. 12 and 13. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 12 and therefore to a reference point of FIG. 13.

As is shown in FIG. 15, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z = SU \quad (2)$$

wherein the matrix Z contains the scores transformed into the LDA space.

Figure 16:
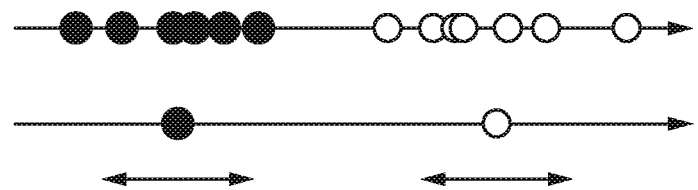
FIG. 16 shows a PCA-LDA space having a single dimension or axis, wherein the LDA is performed based on the PCA space of FIG. 15, the PCA-LDA space comprising plural further transformed reference points or class scores, each further transformed reference point or class score corresponding to a transformed reference point or score of FIG. 15.

FIG. 16 shows a PCA-LDA space having a single dimension or axis, wherein the LDA is performed in the PCA space of FIG. 15. As is shown in FIG. 16, the LDA space comprises plural further transformed reference points or PCA-LDA scores, with each further transformed reference point corresponding to a transformed reference point or PCA score of FIG. 15.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by:

$$V'_g = U^T V_g U \quad (3)$$

wherein $V_g$ are the class covariance matrices in the PCA space.

The transformed class average position $z_g$ for class g may be given by:

$$s_g U = z_g \quad (4)$$

wherein $s_g$ is the class average position in the PCA space.

Multivariate Analysis—Using a Model for Classification

By way of example, a method of using a classification model to classify an aerosol, smoke or vapour sample will now be described.

Figure 17:
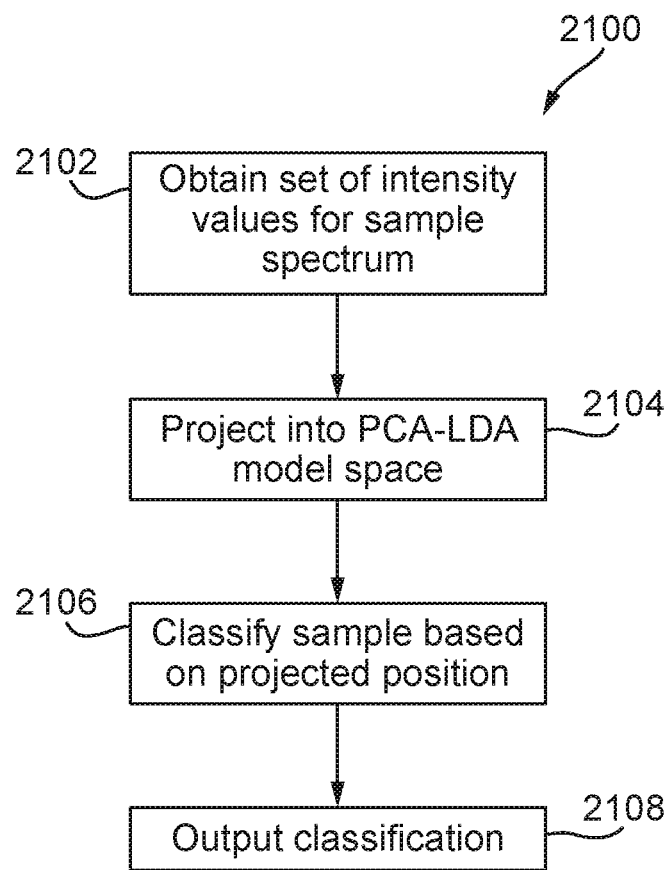
FIG. 17 shows a method of analysis that comprises using a classification model according to various embodiments.

FIG. 17 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

Figure 18:
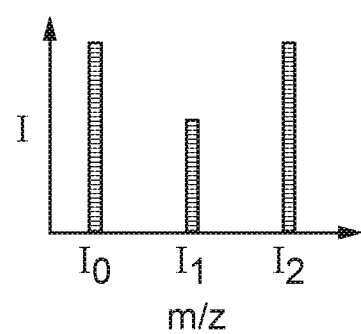
FIG. 18 shows a sample spectrum obtained from an unknown sample.

FIG. 18 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \quad (5)$$

Then, a transformed PCA-LDA vector $z_x$ for the sample spectrum can be obtained as follows:

$$s_x U = z_x \quad (6)$$

Figure 19:
FIG. 19 shows the PCA-LDA space of FIG. 16, wherein the PCA-LDA space further comprises a PCA-LDA projected sample point derived from the peak intensity values of the sample spectrum of FIG. 18.

FIG. 19 again shows the PCA-LDA space of FIG. 16. However, the PCA-LDA space of FIG. 19 further comprises the projected sample point, corresponding to the transformed PCA-LDA vector $z_x$, derived from the peak intensity values of the sample spectrum of FIG. 18.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \quad (7)$$

and the data vector $d_x$ may be assigned to the class for which this distance is smallest.

In addition, treating each class as a multivariate Gaussian, a probability of membership of the data vector to each class may be calculated.

Library Based Analysis—Developing a Library for Classification

By way of example, a method of building a classification library using plural input reference sample spectra will now be described.

Figure 20:
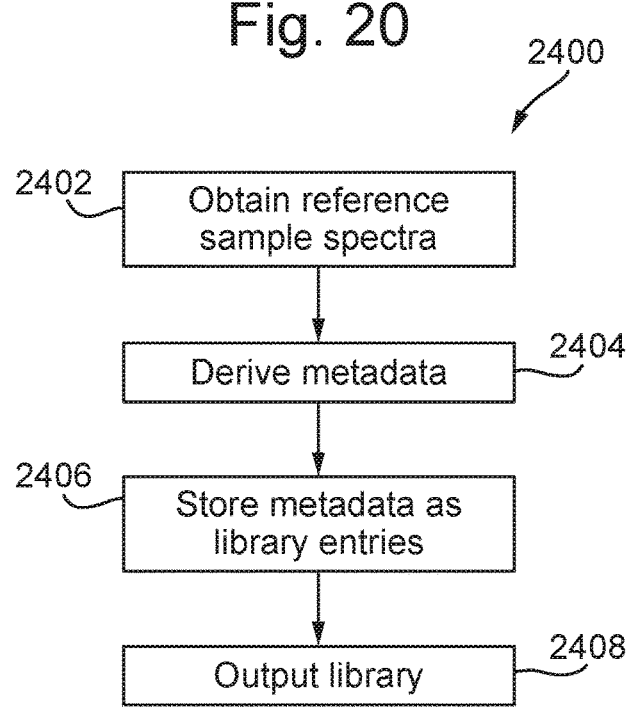
FIG. 20 shows a method of analysis that comprises building a classification library according to various embodiments.

FIG. 20 shows a method 2400 of building a classification library. In this example, the method comprises a step 2402 of obtaining plural input reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \lfloor N_{chan} \log \frac{m}{M_{min}} \big/ \log \frac{M_{max}}{M_{min}} \rfloor \qquad (8)$$

wherein $N_{chan}$ is a selected value and $\lfloor x \rfloor$ denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}_i = 1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i \mid \mu_i, D_i) = \frac{1}{D_i} \frac{C^{C-1/2} \Gamma(C)}{\sqrt{\pi} \, \Gamma(C-1/2)} \frac{1}{\left(C + \frac{(y_i - \mu_i)^2}{D_i^2}\right)^C} \qquad (9)$$

where $\frac{1}{2} \leq C < \infty$ and where $\Gamma(C)$ is the gamma function.

The above equation is a generalised Cauchy distribution which reduces to a standard Cauchy distribution for C=1 and becomes a Gaussian (normal) distribution as C→∞. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i \mid \mu_i, D_i) = \frac{3}{4} \frac{1}{D_i} \frac{1}{(3/2 + (y_i - \mu_i)^2 / D_i^2)^{3/2}} \qquad (10)$$

For each library entry, the parameters $\mu_i$ are set to the median of the list of values in the i'th channel of the input reference sample spectra while the deviation $D_i$ is taken to be the interquartile range of these values divided by $\sqrt{2}$. This choice can ensure that the likelihood for the i'th channel has the same interquartile range as the input data, with the use of quantiles providing some protection against outlying data.

Library Based Analysis—Using a Library for Classification

By way of example, a method of using a classification library to classify an aerosol, smoke or vapour sample will now be described.

Figure 21:
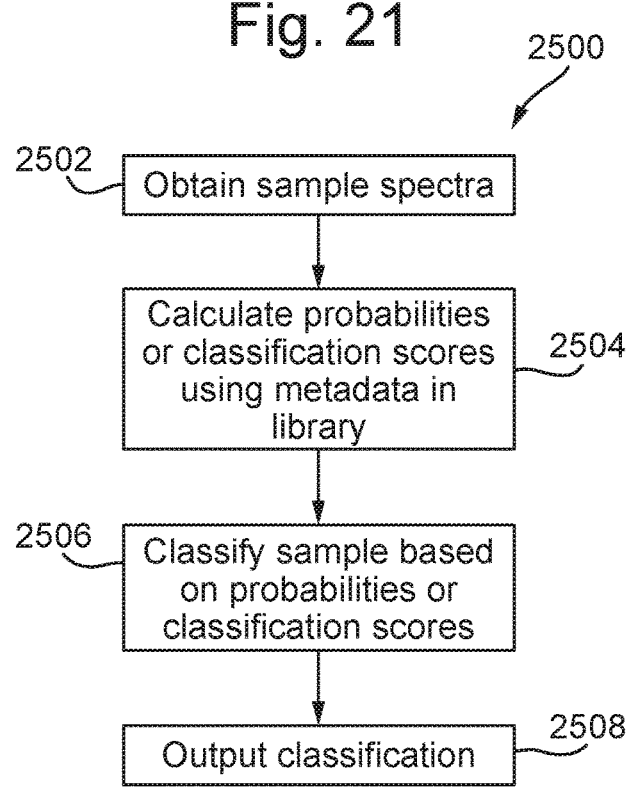
FIG. 21 shows a method of analysis that comprises using a classification library according to various embodiments.

FIG. 21 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y \mid \mu, D) = \prod_{i=1}^{N_{chan}} Pr(y_i \mid \mu_i, D_i) \qquad (11)$$

wherein $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class $\tilde{s}$ is given by:

$$Pr(\tilde{s} \mid y) = \frac{L_{\tilde{s}}^{(1/F)}}{\sum_s L_s^{(1/F)}} \qquad (12)$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}} \qquad (13)$$

Again, the scores $R_s$ are normalised over all candidate classes 's'.

The aerosol, smoke or vapour sample may then be classified as belonging to the class having the highest probability and/or highest RMS classification score.

Non-Surgical Applications

It has also been recognised that a tool comprising a relatively extended and miniaturised probe comprising an ambient ion source for generating aerosol, smoke or vapour from a sample, i.e. similarly to the endoscope described above, may find application outside of the surgical or medical environments.

For instance, such a tool may be used for minimally invasive analysis of fully packed containers e.g. at customs or airport security. The tool may be inserted into a relatively small hole formed in the container, with the ambient ion source then deployed through the tool deployment opening and activated to generate gaseous, smoke or vapour analyte material from within the container, with the gaseous, smoke or vapour material then being aspirated through fenestrations in the tool tubing and transported to an analyser for mass spectrometric analysis. It will be apparent that the endoscope arrangement may be used to detect narcotics or other illegal substances hidden in concealed places.

Similarly, such a tool may find applications for analysis of closed pipe heating or cooling systems. It is known that organic growth such as fungi, bacteria, biofilms and/or algae may clog the heating or cooling pipes, but it is generally difficult to identify the organic material within such systems and hence difficult to ascertain how to treat it. This can be a particular problem in the cooling systems of a nuclear reactor, where disassembly of the cooling system for cleaning is prohibitively time consuming and expensive. By passing the tool through the pipework and deploying the ambient ion source into contact with the obstruction to generate gaseous, smoke or vapour analyte material which can then be aspirated into the tool housing and transported to a mass spectrometer for analysis, it may be possible to identify the nature of the organic growth and hence help determine how best to remove it.

In the same manner, such a tool may find application in the fields of pest/parasite control, or structural testing/surveying. For instance, current methods for analysing fungal growth in the foundations or walls of a house tend to rely on optical imaging methods which can be inconclusive. By probing the growth and then mass analysing the generated gaseous, smoke or vapour analyte material it is possible to more accurately determine the nature of the fungal growth.

The endoscopic tool arrangement may, for example, also be used to probe for asbestos or other potentially hazardous materials in buildings.

Methods of Medical Treatment, Surgery and Diagnosis and Non-Medical Methods

Various different embodiments are contemplated. According to some embodiments the methods disclosed above may be performed on in vivo, ex vivo or in vitro tissue. The tissue may comprise human or non-human animal tissue. Embodiments are contemplated wherein the target may comprise biological tissue, a bacterial or fungal colony or more generally an organic target such as a plastic).

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly (or vice versa) ion mobility analysis (IMS) and/or differential ion mobility analysis (DMA) and/or Field Asymmetric Ion Mobility Spectrometry (FAIMS) analysis followed by secondly (or vice versa) mass analysis by a mass analyser such as a quadrupole mass analyser or a Time of Flight mass analyser. Various embodiments also relate to an ion mobility spectrometer and/or mass analyser and a method of ion mobility spectrometry and/or method of mass analysis. Ion mobility analysis may be performed prior to mass to charge ratio analysis or vice versa.

Various references are made in the present application to mass analysis, mass analysers, mass analysing, mass spectrometric data, mass spectrometers and other related terms referring to apparatus and methods for determining the mass or mass to charge of analyte ions. It should be understood that it is equally contemplated that the present invention may extend to ion mobility analysis, ion mobility analysers, ion mobility analysing, ion mobility data, ion mobility spectrometers, ion mobility separators and other related terms referring to apparatus and methods for determining the ion mobility, differential ion mobility, collision cross section or interaction cross section of analyte ions. Furthermore, it should also be understood that embodiments are contemplated wherein analyte ions may be subjected to a combination of both ion mobility analysis and mass analysis i.e. that both (a) the ion mobility, differential ion mobility, collision cross section or interaction cross section of analyte ions together with (b) the mass to charge of analyte ions is determined. Accordingly, hybrid ion mobility-mass spectrometry (IMS-MS) and mass spectrometry-ion mobility (MS-IMS) embodiments are contemplated wherein both the ion mobility and mass to charge ratio of analyte ions generated e.g. by an ambient ionisation ion source are determined. Ion mobility analysis may be performed prior to mass to charge ratio analysis or vice versa. Furthermore, it should be understood that embodiments are contemplated wherein references to mass spectrometric data and databases comprising mass spectrometric data should also be understood as encompassing ion mobility data and differential ion mobility data etc. and databases comprising ion mobility data and differential ion mobility data etc. (either in isolation or in combination with mass spectrometric data).

Various surgical, therapeutic, medical treatment and diagnostic methods are contemplated.

However, other embodiments are contemplated which relate to non-surgical and non-therapeutic methods of mass spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

Although the present invention has been described with reference to preferred embodiments, it will be understood by those skilled in the art that various changes in form and detail may be made without departing from the scope of the invention as set forth in the accompanying claims.

The invention claimed is:

1. An apparatus for analysis comprising:
a tool comprising an ambient ion source located within a tubing or a housing, wherein said tubing or said housing comprises a tool deployment opening and one or more aspiration ports separate to the tool deployment opening;
a suction device arranged and adapted to aspirate aerosol, smoke or vapour generated using said ambient ion source through said one or more aspiration ports providing in the tubing or housing;
a mass spectrometer and/or ion mobility spectrometer;
tubing which is arranged and adapted to pass said aerosol, smoke or vapour into a vacuum chamber of said mass spectrometer and/or ion mobility spectrometer; and
a collision surface located within a vacuum chamber of said mass spectrometer and/or ion mobility spectrometer arranged such that the aerosol, smoke or vapour passed into the vacuum chamber can then be ionised by colliding with the collision surface;
wherein, through an inlet of the mass spectrometer and/or ion mobility spectrometer, the mass spectrometer and/or ion mobility spectrometer is operative to add a matrix to said aerosol, smoke or vapour prior to said aerosol, smoke or vapour impacting upon said collision surface, wherein said matrix comprises a matrix selected from the group consisting of: (i) an organic solvent; (ii) one or more alcohols; (iii) methanol; (iv) ethanol; (v) isopropanol; (vi) acetone; and (vii) acetonitrile.

2. The apparatus as claimed in claim 1, wherein said ambient ion source comprises a laser device.

3. The apparatus as claimed in claim 1, wherein said ambient ion source is selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

4. The apparatus as claimed in claim 1, wherein said ambient ion source comprises one or more electrodes.

5. The apparatus as claimed in claim 1, wherein said tool comprises either: (i) an electrode which is extendable from and/or retractable within said tubing or housing; (ii) an optical fibre for directing laser radiation on to tissue or another surface, wherein said optical fibre is extendable from and/or retractable within said tubing or housing; (iii) an argon plasma coagulation device or a hybrid argon plasma coagulation device; or (iv) a water jet device or a hydrosurgical or surgical water jet device.

6. The apparatus as claimed in claim 1, further comprising an endoscope.

7. The apparatus as claimed in claim 6, wherein said endoscope comprises a port, wherein said tool configured to be deployed through said port.

8. The apparatus as claimed in claim 1, wherein said suction device is arranged and adapted to aspirate said aerosol, smoke or vapour through said one or more aspiration ports in a substantially continuous manner.

9. The apparatus as claimed in claim 1, wherein said suction device is arranged and adapted to aspirate said aerosol, smoke or vapour through said one or more aspiration ports in a substantially pulsed, discontinuous or irregular manner.

10. The apparatus as claimed in claim 1, further comprising a heating device which is arranged and adapted to heat said collision surface.

11. The apparatus as claimed in claim 1, further comprising an alarm which is arranged and adapted to:
receive an indication of a type of tissue being analyzed by the mass spectrometer and/or ion mobility spectrometer, and
generate feedback responsive to the tissue being from an undesired target region or area.

12. The apparatus as claimed in claim 1, further comprising an analysis device for analysing one or more sample spectra so as to classify said aerosol, smoke or vapour sample using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; and (xxii) subspace discriminant analysis.

13. The apparatus as claimed in claim 1, wherein the matrix comprises isopropanol.

14. An apparatus for analysis comprising:
a tool comprising an ambient ion source located within a tubing or a housing, wherein said tubing or said housing comprises a tool deployment opening and one or more aspiration ports separate to the tool deployment opening;
a suction device arranged and adapted to aspirate aerosol, smoke or vapour generated using said ambient ion source through said one or more aspiration ports providing in the tubing or housing; and
a mass spectrometer and/or ion mobility spectrometer;
the apparatus further comprising:
tubing which is arranged and adapted to pass said aerosol, smoke or vapour into a vacuum chamber of said mass spectrometer and/or ion mobility spectrometer;
a collision surface located within a vacuum chamber of said mass spectrometer and/or ion mobility spectrometer arranged such that the aerosol, smoke or vapour passed into the vacuum chamber can then be ionised by colliding with the collision surface; and
an interface to a matrix for adding the matrix to said aerosol, smoke or vapour, wherein said matrix is added, in use, to said aerosol, smoke or vapour prior to said aerosol, smoke or vapour impacting upon said collision surface, wherein said matrix comprises a matrix selected from the group consisting of: (i) an organic solvent; (ii) one or more alcohols; (iii) methanol; (iv) ethanol; (v) isopropanol; (vi) acetone; and (vii) acetonitrile.

15. An apparatus for analysis comprising:
a tool comprising an ambient ion source located within a tubing or a housing, wherein said tubing or said housing comprises a tool deployment opening and one or more aspiration ports separate to the tool deployment opening;
a suction device arranged and adapted to aspirate aerosol, smoke or vapour generated using said ambient ion source through said one or more aspiration ports providing in the tubing or housing; and
a mass spectrometer and/or ion mobility spectrometer;
tubing which is arranged and adapted to pass said aerosol, smoke or vapour into a vacuum chamber of said mass spectrometer and/or ion mobility spectrometer; and
a collision surface located within a vacuum chamber of said mass spectrometer and/or ion mobility spectrometer arranged such that the aerosol, smoke or vapour passed into the vacuum chamber can then be ionised by colliding with a collision surface;
wherein, through an inlet of the mass spectrometer and/or ion mobility spectrometer, the mass spectrometer and/or ion mobility spectrometer is operative to add a matrix to form a mixture with said aerosol, smoke or vapour to dissolve analyte molecules within said aerosol, smoke or vapour, prior to causing the mixture to impact upon said collision surface, wherein said matrix comprises a matrix selected from the group consisting of: (i) an organic solvent; (ii) one or more alcohols; (iii) methanol; (iv) ethanol; (v) isopropanol; (vi) acetone; and (vii) acetonitrile.

* * * * *